United States Patent
Perlman

(10) Patent No.: US 9,504,796 B2
(45) Date of Patent: Nov. 29, 2016

(54) REDUCING VENTILATOR-INDUCED LUNG INJURY

(71) Applicant: The Trustees of the Stevens Institute of Technology, Hoboken, NJ (US)

(72) Inventor: Carrie E. Perlman, New York, NY (US)

(73) Assignee: THE TRUSTEES OF THE STEVENS INSTITUTE OF TECHNOLOGY, Hoboken, NJ (US)

( * ) Notice: Subject to any disclaimer, the term of this patent is extended or adjusted under 35 U.S.C. 154(b) by 786 days.

(21) Appl. No.: 13/650,759

(22) Filed: Oct. 12, 2012

(65) Prior Publication Data

US 2013/0092167 A1 Apr. 18, 2013

Related U.S. Application Data

(60) Provisional application No. 61/547,133, filed on Oct. 14, 2011.

(51) Int. Cl.
*A61M 16/00* (2006.01)
*A61M 16/20* (2006.01)

(52) U.S. Cl.
CPC ..... *A61M 16/0051* (2013.01); *A61M 16/0006* (2014.02); *A61M 16/0009* (2014.02); *A61M 16/0096* (2013.01); *A61M 16/205* (2014.02); *A61M 16/209* (2014.02); *A61M 16/00* (2013.01); *A61M 16/0054* (2013.01); *A61M 2016/0027* (2013.01); *A61M 2202/0488* (2013.01); *A61M 2210/1039* (2013.01)

(58) Field of Classification Search
CPC ........... A61M 16/00; A61M 16/0054; A61M 2202/0488; A61M 2210/1039
See application file for complete search history.

(56) References Cited

U.S. PATENT DOCUMENTS

| | | | |
|---|---|---|---|
| 4,216,776 A | 8/1980 | Downie | |
| 6,180,142 B1 | 1/2001 | Taeusch | |
| 8,967,144 B2 | 3/2015 | Lurie | |
| 2009/0208581 A1* | 8/2009 | Edwards | A61K 9/0075 424/489 |

OTHER PUBLICATIONS

Varisco, B. M. (2011). The pharmacology of acute lung injury in sepsis. Advances in pharmacological sciences, 2011.*
Gu, J., & Korteweg, C. (2007). Pathology and pathogenesis of severe acute respiratory syndrome. The American journal of pathology, 170(4), 1136-1147.*

(Continued)

*Primary Examiner* — Imani Hayman
*Assistant Examiner* — Nilay Shah
(74) *Attorney, Agent, or Firm* — Greenberg Traurig, LLP

(57) ABSTRACT

Methods are provided for protecting against ventilation-induced lung injury both directly, by lowering surface tension, and indirectly, by promoting equitable liquid distribution in pulmonary alveolar edema, in which liquid- and air-filled alveoli are normally interspersed. Since a pressure barrier is responsible for trapping liquid in discrete edematous alveoli and the magnitude of the barrier is proportional to surface tension at the air-liquid interface, the present invention provides various methods for promoting equitable redistribution of edema liquid amongst alveoli to help protect the lung during ventilation, including: i) use of an additive that lowers surface tension; ii) use of active, accelerated deflation during mechanical ventilation; and iii) high frequency (>50 Hz) vibration of the lung.

8 Claims, 15 Drawing Sheets

(56) References Cited

OTHER PUBLICATIONS

Polat, B. E., Lin, S., Mendenhall, J. D., VanVeller, B., Langer, R., & Blankschtein, D. (2011). Experimental and molecular dynamics investigation into the amphiphilic nature of sulforhodamine B. The Journal of Physical Chemistry B, 115(6), 1394-1402.*
National Center for Biotechnology Information. PubChem Compound Database; CID=65191, https://pubchem.ncbi.nlm.nih.gov/compound/65191 (accessed May 6, 2016).*
Wang, Z. et al., Acylation of Pulmonary Surfactant Protein-C Is Required for Its Optimal Surface Active Interactions with Phospholipids, The Journal of Biological Chemistry, vol. 271, No. 32, (1996), 19104-19109.
Ware, L. et al., The acute respiratory distress syndrome, N Engl J Med, 342: 1334-1349, 2000.
Warr, R. et al., Low molecular weight human pulmonary surfactant protein (SP5): Isolation, characterization, and cDNA and amino acid sequences, Proc Natl Acad Sci USA, vol. 84, (1987), 7915-7919.
Warriner, H. et al., A concentration-dependent mechanism by which serum albumin inactivates replacement lung surfactants, Biophys J, 82: 835-842, 2002.
Weg, J. et al., Safety and potential efficacy of an aerosolized surfactant in human sepsis-induced adult respiratory distress syndrome, JAMA, 272: 1433-1438, 1994.
Whitsett, J. et al., Hydrophobic Surfactant-Associated Protein in Whole Lung Surfactant and Its Importance for Biophysical Activity in Lung Surfactant Extracts Used for Replacement Therapy, Pediatric Research, vol. 20, No. 5, (1986), 460-467.
Willson, D. et al., Surfactant for Pediatric Acute Lung Injury, Pediatr Clin N Am, 55, (2008), 545-575.
Willson, D. et al., Effect of exogenous surfactant (calfactant) in pediatric acute lung injury: a randomized controlled trial, JAMA, 293: 470-476, 2005.
Wu, Y. et al., Lung ventilation injures areas with discrete alveolar flooding, in a surface tension-dependent fashion, J Appl Physiol, 117: 788-796, 2014.
Yapicioglu, H. et al., The use of surfactant in children with acute respiratory distress syndrome: efficacy in terms of oxygenation, ventilation and mortality, Pulmonary Pharmacology & Therapeutics, 16, (2003), 327-333.
Yu, S. S et al., Reconstitution of surfactant activity by using the 6 kDa apoprotein associated with pulmonary surfactant, . Biochem J, 236, (1986), 85-89.
Yu, S. et al., Characterization of the small hydrophobic proteins associated with pulmonary surfactant, Biochimica et Biophysica Acta, vol. 921, No. 3, (1987), 437-448.
Yu, S. et al., Role of bovine pulmonary surfactant-associated proteins in the surface-active property of phospholipid mixtures, Biochim Biophys Acta, 1046: 233-241, 1990.
Yu, S. et al., Effect of pulmonary surfactant protein A and neutral lipid on accretion and organization of dipalmitoylphosphatidycholine in surface films, Journal of Lipid Research, vol. 37, (1996), 1278-1288.
Zasadzinski, J. et al., Inhibition of pulmonary surfactant adsorption by serum and the mechanisms of reversal by hydrophilic polymers: theory, Biophys J, 89: 1621-1629,2005.
Zasadzinski, J. et al., Overcoming rapid inactivation of lung surfactant: Analogies between competitive adsorption and colloid stability, Biochimica et Biophysica Acta, 1798, (2010), 801-828.
Liau, D. et al., Functional Abnormalities of Lung Surfactant in Experimental Acute Alveolar Injury in the Dog, Am Rev Respir Dis, 136, (1987), 395-401.
Lukovic, D. et al., Production and characterisation of recombinant forms of human pulmonary surfactant protrain C (SP-C): Structure and surfact activity, Biochimica et Biophysica Acta, 1758, (2006), 509-518.
Mazela, J. et al,. Comparison of poractant alfa and lyophilized lucinactant in a preterm lamb model of acute respiratory distress, Pediatric Research, vol. 72, No. 1, (2012), 32-37.
Moison, R. et al., Plasma Proteins in Acute and Chronic Lung Disease of the Newborn, Free Radical Biology & Medicine, vol. 25, No. 3, (1998), 321-328.
Morley, C., Systematic review of prophylactic vs rescue surfactant, Archives of Disease in Childhood, 77, (1997), F70-F74.
Nakamura, H. et al., Monomolecular surface film and tubular myelin figures of the pulmonary surfactant in hamster lung, Cell Tissue Res, 241, (1985), 523-528.
Nicholas, T. Pulmonary Surfactant: No mere paint on the alveolar wall, Respirology, 1, (1996), 247-257.
Niemarkt, H. et al., Effects of less-invasive surfactant administration on oxygenation, pulmonary surfactant distribution, and lung compliance in spontaneously breathing preterm lamb, Pediatric Research, 76, (2014), 166-170.
Notter, R. et al., Biophysical Activity of Synthetic Phospholipids Combined with Purified Lung Surfactant 6000 Dalton Apoprotein, Chemistry and Physics of Lipids, 44, (1987) 1-17.
Otsubo, E. et al., Characterization of the Surface Activity of a Synthetic Surfactant with Albumin, Biol Pharm Bull, 25 (12), (2002), 1519-1523.
Petty, T. et al., Abnormalities in Lung Elastic Properties and Surfactant Function in Adult Respiratory-Distress Syndrome. Chest 75: 571-574,1979.
Petty, T. et al., Characteristics of Pulmonary Surfactant in Adult Respiratory Distress Syndrome Associated with Trauma and Shock, American Review of Respiratory Disease, 115, (1977), 531-536.
Phua, J. et al., Has mortality from acute respiratory distress syndrome decreased over time?: A systematic review, Am J Respir Crit Care Med, 179: 220-227, 2009.
Pison, U. et al., Surfactant Abnormalities in Patients with Respiratory Failure after Multiple Trauma, Am Rev Respir Dis, 140: 1033-1039, 1989.
Plasencia, I. et al., The N-terminal segment of pulmonary surfactant lipopeptide SP-C hasintrinsic propensity to interact with and perturb phospholipid bilayers, Biochem J, 377, (2004), 183-193.
Polat, B. et al., An experimental and molecular dynamics investigation into the amphiphilic nature of sulforhodamine B, J Phys Chem B, 115: 1394-1402, 2011.
Product Monograph, Curosurf, Chiesi Farmaceutici, Parma, Italy, Sep. 2009.
Robertson, B. et al., Principles of surfactant replacement, Biochimica et Biophysica Acta, 1408, (1998) 346-361.
Rooney, S., Lung Surfactant, Environmental Health Perspectives, 55, (1984), 205-226.
Rubenfeld, G. et al., Incidence and outcomes of acute lung injury, N Engl J Med, 353: 1685-1693, 2005.
Sarin, V. et al., Biophysical and biological activity of a synthetic 8.7-kDa hydrophobic pulmonary surfactant protein SP-B, Proc Natl Acad Sci USA, 87, (1990), 2633-2637.
Schmidt, R. et al., Alteration of fatty acid profiles in different pulmonary surfactant phospholipids in acute respiratory distress syndrome and severe pneumonia, Am J Respir Crit Care Med, 163: 95-100, 2001.
Scientific Committee on Consumer Products (SCCP), Health and Consumer Protection Directorate-General, European Commission. Opinion on Acid Red 52 (Online). http://ec.europa.eu/health/ph_risk/committees/04_sccp/docs/sccp_o_137.pdf [Jun. 24, 2008].
Seeger, W. et al., Alveolar surfactant and adult respiratory distress syndrome, Clin Investig, 71, (1993), 177-190.
Seeger, W. et al., Surfactant inhibition by plasma proteins: differential sensitivity of various surfactant preparations, Eur Respir J, 6, (1993), 971-977.
Seeger, W. et al., Differential sensitivity to fibrinogen inhibition of SP-C- vs. SP-B-based surfactants, Am J Physiol Lung Cell Mol Physiol, 262: L286-L291, 1992.
Seeger, W. et al., Alteration of surfactant function due to protein leakage: special interaction with fibrin monomer, J Appl Physiol, 58: 326-338, 1985.
Seehase, M. et al., New Surfactant with SP-B and C Analogs Gives Survival Benefit after Inactivation in Preterm Lambs, PLoS One, 7(10), (2012), e47631.

(56) References Cited

OTHER PUBLICATIONS

Segerer, H. et al., Rapid Tracheal Infusion of Surfactant versus Bolus Instillation in Rabbits: Effects on Oxygenation, Blood Pressure and Surfactant Distribution, Biol Neonate, 69, (1996), 119-127.
Smart, P. et al., An Evaluation of Some Fluorescent Dyes for Water Tracing, Water Resources Research, vol. 13, No. 1, (1977), 15-33.
Smart, P., A review of the toxicity of twelve fluorescent dyes used for water tracing, NSS Bulletin, 46: 21-33, 1984.
Speer, C. et al., Early versus late surfactant therapy in severe respiratory distress syndrome, Lung, Suppl, (1990), 870-876.
Spragg, R. et al., Effect of recombinant surfactant protein C-based surfactant on the acute respiratory distress syndrome, N Engl J Med, 351: 884-892, 2004.
Spragg, R. et al., Surfactant Replacement Therapy, Clinics in Chest Medicine, vol. 21, No. 3, (2000), 531-541.
Spragg, R. et al., Recombinant surfactant protein C-based surfactant for patients with severe direct lung injury, Am J Respir Crit Care Med, 183: 1055-1061, 2011.
St. Clair, C. et al., The Probability of Neonatal Respiratory Distress Syndrome as a Function ofGestational Age and Lecithin/Sphingomyelin Ratio, American Journal of Perinatology, vol. 25, No. 8, (2008), 473-480.
Szyperski, T. et al., Pulmonary surfactant-associated polypeptide C in a mixed organic solvent transforms from a monomeric a-helical state into insoluble P-sheet aggregates, Protein Science, 7, (1998), 2533-2540.
Taeusch, H. et al., Inactivation of pulmonary surfactant due to serum-inhibited adsorption and reversal by hydrophilic polymers: Experimental, Biophys J, 89: 1769-1779, 2005.
Takahashi, A. et al., Structure-function relationships of bovine pulmonary surfactant proteins: SP-B and SP-C, Biochim Biophys Acta, 1044: 43-49, 1990.
Tanaka, Y. et al., Lung Surfactants. II. Effects of fatty acids, triacylglycerols and protein on the activity of lung surfactant, Chemical and Pharmaceutical Bulletin, vol. 31, No. 11, (1983), 4100-4109.
Terry, M. et al., Pulmonary Distribution of Lucinactant and Poractant Alfa and Their Peridosing Hemodynamic Effects in a Preterm Lamb Model of Respiratory Distress Syndrome, Pediatric Research, vol. 68, No. 3, (2010), 193-198.
Tierney, D. et al., Altered surface tension of lung extracts and lung mechanics, J Appl Physiol, 20: 1253-1260, 1965.
Tsuda, S. et al., DNA damage induced by red food dyes orally administered to pregnant and male mice, Toxicol Sci, 61: 92-99, 2001.
Ueda, T. et al., Distribution of surfactant and ventilation in surfactant-treated preterm lambs, Journal of Applied Physiology, vol. 76, No. 1, (1994), 45-55.
Veldhuizen, R. et al., Pulmonary surfactant subfractions in patients with the acute respiratory distress syndrome, Am J Respir Crit Care Med, 152: 1867-1871, 1995.
Von Nahmen, A. et al., The phase behavior of lipid monolayers containing pulmonary surfactant protein C studied by fluorescence light microscopy, Eur Biophys, J, 26, (1997), 359-369.
Voss, T. et al., Primary structure differences of human and surfactant-associated proteins isolated from normal and proteinosis lung, Biochimica et Biophysica Acts, 1138, (1992), 261-267.
Walther, F. et al., Hydrophobic Surfactant Proteins and Their Analogues, Neonatology, 91, (2007), 303-310.
Walther, F. et al., A Synthetic Segment of Surfactant Protein A: Structure, in Vitro Surface Activity, and in Vivo Efficacy, Pediatric Research, 39(6), (1996), 938-946.
Amizuka, T. et al., Surfactant therapy in neonates with respiratory failure due to haemorrhagic pulmonary oedema, Eur J Pediatr, 162, (2003), 697-702.
Anzueto, A. et al., Aerosolized Surfactant in Adults with Sepsis-Induced Acute Respiratory Distress Syndrome. New Engl J Med 334: 1417-1422, 1996.

Banerjee, R. et al., Ultrastructure of exogenous surfactants using cryogenic scanning electron microscopy, J Biomater Appl, 15, (2001), 230-240.
Batenburg, J. et al., The lipids of pulmonary surfactant: dynamics and interactions with proteins. Prog Lipid Res 37: 235-276,1998.
Baumgart, F. et al., Palmitoylation of Pulmonary Surfactant Protein SP-C is Critical for Its Functional Cooperation with SP-B to Sustain Compression/Expansion Dynamics in Cholesterol-Containing Surfactant Films, Biophysical Journal, 99, (2010), 3234-3243.
Bernhard, W. et al., Commercial versus Native Surfactants: Surface Activity, Molecular Components, and the Effect of Calcium, Am J Respir Crit Care Med, 162, (2000) 1524-1533.
Berry, D. et al., Respiratory distress and surfactant inhibition following vagotomy in rabbits, J Appl Physiol, 61, (1986), 1741-1748.
Bradbury, J., Could treatment of neonatal RDS improve further?, The Lancet, 360, (2002), p. 394.
Braun, A. et al., A Freeze-Fracture Transmission Electron Microscopy and Small Angle X-Ray Diffraction Study of the Effects of Albumin, Serum and Polymers on Clinical Lung Surfactant Microstructure, Biophysical Journal, 93, (2007) 123-139.
Brower, R.G. et al., The Acute Respiratory Distress Syndrome Network. Ventilation with lower tidal volumes as compared with traditional tidal volumes for acute lung injury and the acute respiratory distress syndrome. N Engl J Med 342: 1301-1308, 2000.
Cassidy, K. et al., Liquid Plug Flow in Straight and Bifurcating Tubes, Journal of Biomechanical Engineering, 123, (2001), 580-589.
Clements, J., Lung Surfactant: A Personal Perspective, Annu Rev Physiol, 59, (1997) 1-21.
Curstedt, T. et al., Different Effects of Surfactant Proteins B and C—Implications for Development of Synthetic Surfactants, Neonatology, 97, (2010), 367-372.
De Prost, N. et al., Ventilator-induced lung injury: historical perspectives and clinical implications, Annals of Intensive Care, 1:28, (2011), 1-15.
Dhar, P. et al., Liquid Protein Interactions Alter Line Tensions and Domain Size Distributions in Lung Surfactant Monolayers, Biophysical Journal, 102, (2012), 56-65.
Diemel, R. et al., In vitro and in vivo intrapulmonary distribution of fluorescently labeled surfactant, Crit Care Med, vol. 30, No. 5, (2002), 1083-1090.
"Dijk, P. et al., A Comparison of the Hemodynamic and Respiratory Effects of Surfactant Instillation during Interrupted Ventilationversus Noninterrupted Ventilation in Rabbits with Severe Respiratory Failure, Pediatric Research, 45(2), (1999), 235-241".
"Ding, J. et al., Effects of Lung Surfactant Proteins, SP-B and SP-C, and Palmitic Acid onMonolayer Stability, Biophysical Journal, 80, (2001), 2262-2272".
Dluhy, R. et al., Deacylated Pulmonary Surfactant Protein SP-C Transforms From a-Helical to Amyloid Fibril Structure via a pH-Dependent Mechanism: An Infrared Structural Investigation, Biophysical Journal, 85, (2003), 2417-2429.
Dreyfuss, D. et al., Ventilator-induced lung injury: lessons from experimental studies. Am J Respir Crit Care Med 157: 294-323,1998.
Goss, C. et al., Incidence of acute lung injury in the United States, Crit Care Med, vol. 31, No. 6, (2003), 1607-1611.
Greenough, A. Expanded use of surfactant replacement therapy, Eur J Pediatr, 159, (2000), 635-640.
Gregory, T. et al., Surfactant chemical composition and biophysical activity in acute respiratory distress syndrome. J Clin Invest, 88, (1991), 1976-1981.
Gregory, T. et al., Bovine surfactant therapy for patients with acute respiratory distress syndrome, Am J Respir Crit Care Med, 155, (1997), 1309-1315.
Gunther, A. et al., Surfactant alterations in severe pneumonia, acute respiratory distress syndrome, and cardiogenic lung edema. Am J Respir Crit Care Med 153: 176-184, 1996.
Gustafsson, M. et al., Amyloid fibril formation by pulmonary surfactant protein C, FEBS Letters, 464, (1999), 138-142.

(56) References Cited

OTHER PUBLICATIONS

Gustafsson, M. et al., Palmitoylation of a pulmonary surfactant protein C analogue affects the surface associated lipid reservoir and film stability, Biochimica et Biophysica Acta, 1466 (2000) 169-178.
Gustafsson, M. et al., The Palmitoyl Groups of Lung Surfactant Protein C Reduce Unfolding into a Fibrillogenic Intermediate, J Mol Biol, 310, (2001), 937-950.
Hall, S. et al., Changes in Subphase Aggregates in Rabbits Injured by Free Fatty Acid, Am J Respir Crit Care Med, 149, (1994) 1099-1106.
Halliday, H., Surfactants: past, present and future. J Perinatol 28, Suppl 1: S47-S56, 2008.
Hallman, M. et al., Evidence of lung surfactant abnormality in respiratory failure. Study of bronchoalveolar lavage phospholipids, surface activity, phospholipase activity, and plasma myoinositol, J Clin Invest, 70: 673-683, 1982.
Heldt, G. et al., Distribution of Surfactant, Lung Compliance, and Aeration of Preterm Rabbit Lungs after Surfactant Therapy and Conventional and High-Frequency Oscillatory Ventilation, Pediatric Research, vol. 31, No. 3, (1992), 270-275.
Henry, M. et al., Ultrasonic Nebulized in Comparison with Instilled Surfactant Treatment of Preterm Lambs, Am J Respir Crit Care Med, 154, (1996), 366-375.
Holm, B. et al., Content of Dipalmitoyl Phosphatidylcholine in Lung Surfactant: Ramifications for Surface Activity, Pediatric Research, 39(5), (1996), 805-811.
Holm, B. et al., A biophysical mechanism by which plasma proteins inhibit lung surfactant activity, Chem Phys Lipids, 49, (1988) 49-55.
Ikegami, M. et al., A Protein That Inhibits Surfactant in Respiratory Distress Syndrome, Biol Neonate, 50, (1986), 121-129.
Jobe, A. et al., Lung protein leaks in ventilated lambs: effects of gestational age, Journal of Applied Physiology, vol. 58, No. 4, (1985), 1246-1251.
Jobe, A. et al., Permeability of premature lamb lungs to protein and the effect of surfactant on that permeability, Journal of Applied Physiology, vol. 55, No. 1, (1983), 169-176.
Johansson, J. et al., Molecular structures and interactions of pulmonary surfactant components, Eur J Biochem 244: 675-693, 1997.
Jordanova, A. et al., Influence of surfactant protein C on the interfacial behavior of phosphatidylethanolamine monolayers, Eur Biophys J, 38, (2009), 369-379.
Kesecioglu, J. et al., Exogenous natural surfactant for treatment of acute lung injury and the acute respiratory distress syndrome, Am J Respir Crit Care Med, 180: 989-994, 2009.
Kharge, A. et al., Sulforhodamine B interacts with albumin to lower surface tension and protect against ventilation injury of flooded alveoli. J Appl Physiol, 118, (2015), 355-364.
Kharge, A. et al., Surface tension in situ in flooded alveolus unaltered by albumin, J Appl Physiol, 117: 440-451, 2014.
Kitamura, M. et al., Binding of sulforhodamine B to human serum albumin: a spectroscopic study, Dyes Pigments, 99: 588-593,2013.
Kovacs, H. et al., The Effect of Environment on the Stability of an Integral Membrane Helix: Molecular Dynamics Simulations of Surfactant Protein C in Chloroform, Methanol and Water, J Mol Biol, 247, (1995), 808-822.
Krause, M. et al., Alveolar Recruitment Promotes Homogeneous Surfactant Distribution in a Piglet Model of Lung Injury, Pediatric Research, vol. 50, No. 1, (2001), 34-43.
Landmann, E. et al., Protein content and biophysical properties of tracheal aspirates form nennates with respiratory failure, Klin Padiatr, 214, (2002), 1-7.
Lewis, J. et al., Altered Alveolar Surfactant Is an Early Marker of Acute Lung Injury in Septic Adult Sheep, American Journal of Respiratory and Critical Care Medicine, vol. 150, No. 1, (1994), 123-130.
Lewis, J. et al., Lung function and surfactant distribution in saline-lavaged sheep given instilled vs. nebulized surfactant, Journal of Applied Physiology, vol. 74, No. 3, (1993), 1256-1264.
Li, J. et al., The N-terminal Propeptide of Lung Surfactant Protein C is Necessary for Biosynthesis and Prevents Unfolding of a Metastable a-Helix, J Mol Biol, 338, (2004), 857-862.
Wilkins et al., "Egan's Fundamentals of Respiratory Care", Mosby, Inc. (2009), pp. 939-941.
Bachofen et al., "Experimental Hydrostatic Pulmonary Edema in Rabbit Lungs", The American Review of Respiratory Disease, vol. 147, (1993), pp. 989-996.
Brower et al., "Another "Negative" Trial of Surfactant, Time to Bury this Idea?", American Journal of Respiratory and Critical Care Medicine, vol. 183, (2011), pp. 966-968.
Krishnan et al., "High-Frequency Ventilation for Acute Lung Injury and ARDS", Chest, vol. 118, No. 3, Sep. 2000, pp. 795-807.
Perlman et al., "Micromechanics of Alveolar Edema", American Journal of Respiratory Cell Molecular Biology, vol. 44, (2011) pp. 34-39.
Staub et al., "Pulmonary edema in dogs, especially the sequence of fluid accumulation in lungs", Journal of Applied Physiology, vol. 22, No. 2, (1967), pp. 227-240.
Stawicki et al., "High-Frequency Oscillatory Ventilation (HFOV) and Airway Pressure Release Ventilation (APRV): A Practical Guide", Journal of Intensive Care Medicine, vol. 24, No. 4, Jul./Aug. 2009, pp. 215-229.
Tsuchida et al., "Atelectasis Causes Alveolar Injury in Nonatelectatic Lung Regions", American Journal of Respiratory Critical Care Medicine, vol. 174, (2006), pp. 279-289.
Cario et al., "Mosby's Respiratory Care Equipment (Eighth Edition)", 2011, pp. 217-228; 233-238; 377; 398-403 and 685.
Walther, F., et al. (2014), Surfactant protein C peptides with salt-bridges ("ion-locks") promote high surfactant activities by mimicking the α-helix and membrane topography of the native protein. PeerJ 2:e485; DOI 10.7717/peerj.485, published Jul. 15, 2014.

\* cited by examiner $$P_{LIQ-EDEM} = P_{ALV} - 2T/R_{MENISC}$$
$$\Delta P_{BARRIER} = P_{LIQ-BORD} - P_{LIQ-EDEM} = 2T(1/R_{MENISC} - 1/R_{BORD}) > 0$$

Baseline | Five Ventilation Cycles | 0 min | 5 min | 10 min
Time Post Ventilation
(Constant 5 cmH$_2$O Inflation Pressure)

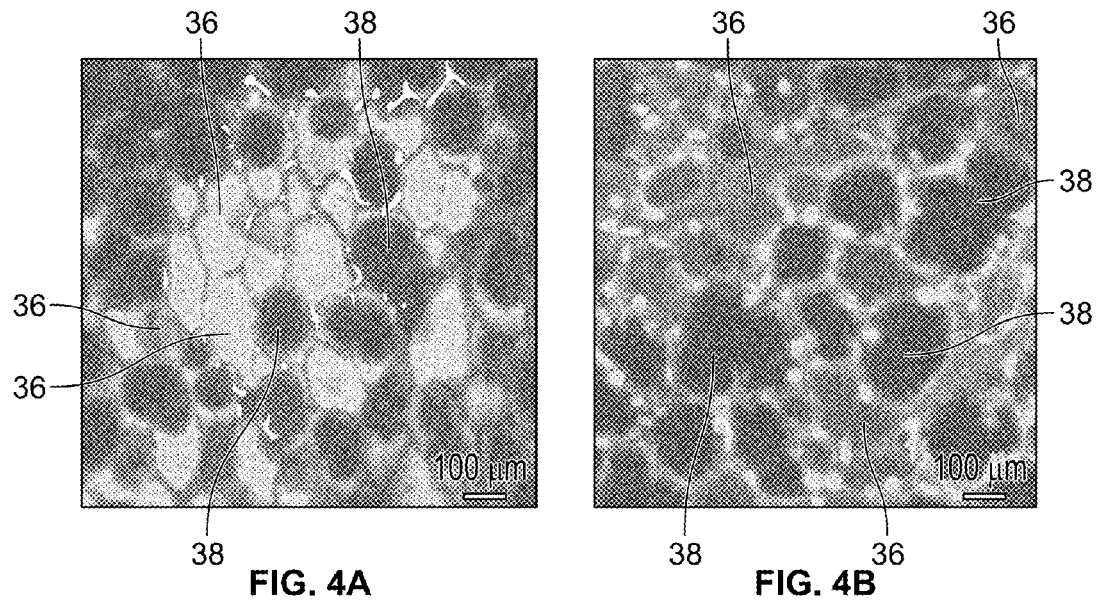
FIG. 4A    FIG. 4B
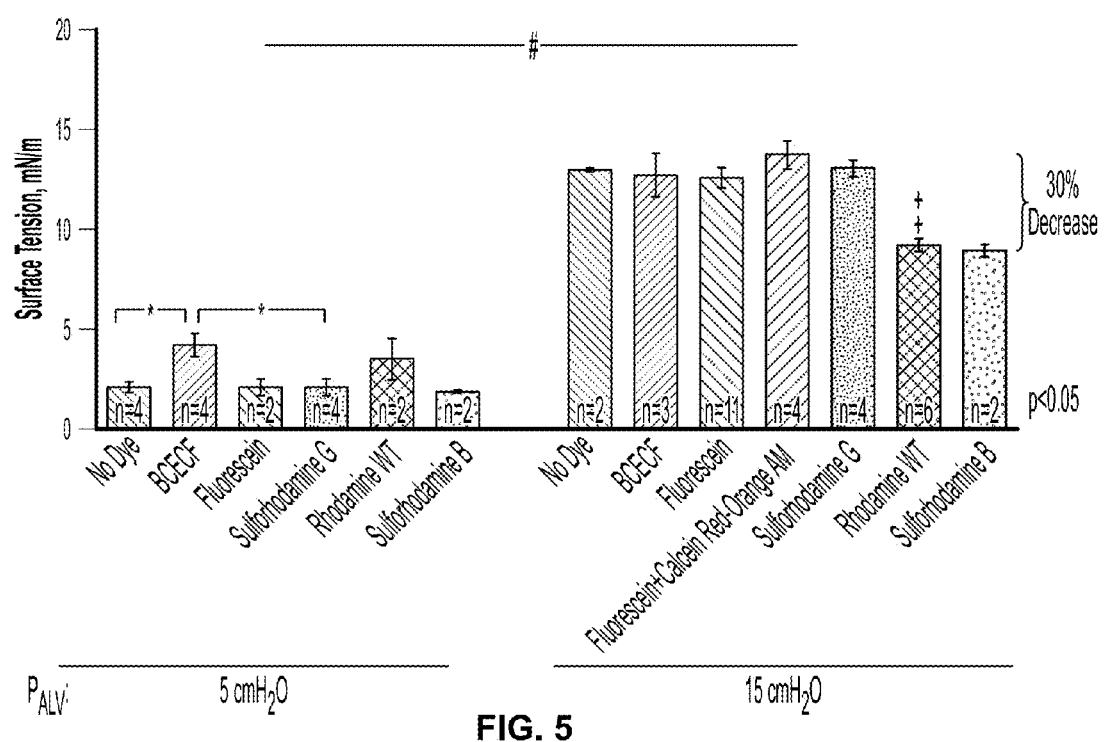
FIG. 5

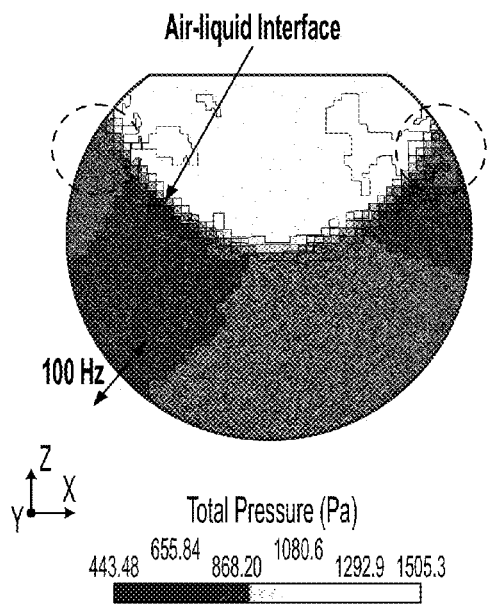
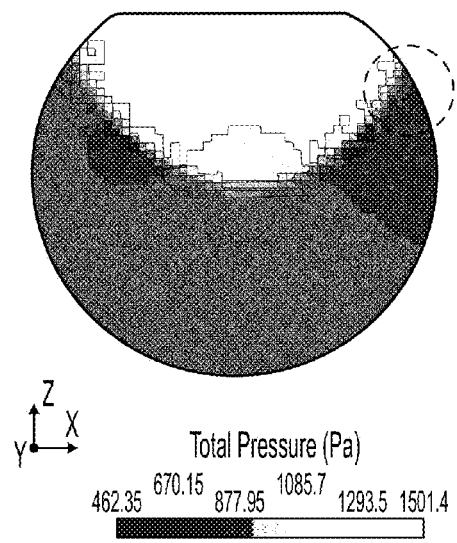
FIG. 12A
FIG. 12B
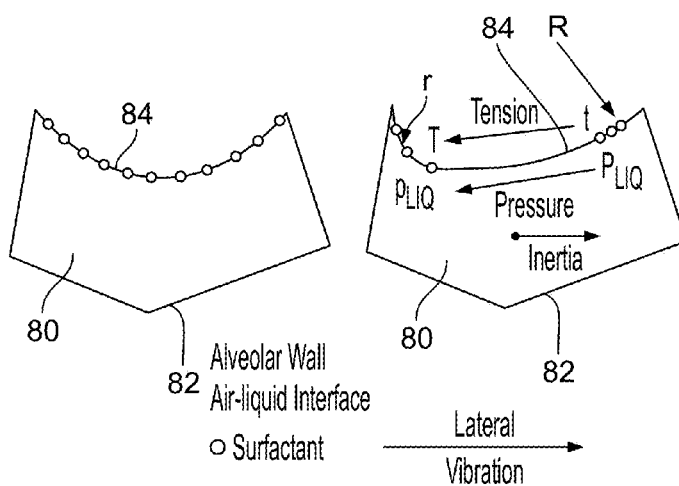
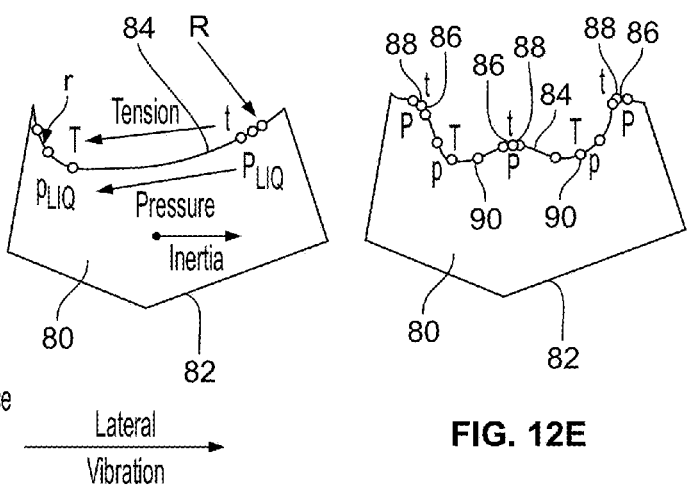
FIG. 12C
FIG. 12D
FIG. 12E

REDUCING VENTILATOR-INDUCED LUNG INJURY

CROSS-REFERENCE TO RELATED APPLICATIONS

The present application claims the benefit of U.S. Provisional Patent Application No. 61/547,133, filed on Oct. 14, 2011, which is incorporated herein in its entirety.

FIELD OF THE INVENTION

The present invention relates to a means of reducing surface tension in the lung and methods for promoting equitable liquid distribution amongst pulmonary alveoli in the presence of alveolar edema, all of which contribute to reducing ventilator-induced lung injury.

BACKGROUND OF THE INVENTION

Physiology and Pathophysiology

Lung Physiology.

The terminal airspaces of the lungs, the alveoli, are lined with a thin liquid layer. Thus there is an air-liquid interface in the lungs that has an associated surface tension. To reduce the surface tension, alveolar type II epithelial cells release surfactant—an aggregate of phospholipids and proteins—into the liquid lining layer. The surfactant adsorbs to and reduces surface tension at the air-liquid interface. By lowering surface tension, surfactant reduces the pressure required to keep the lungs inflated and reduces the work of breathing.

ALI/ARDS.

Acute lung injury (ALI) and its more severe form, acute respiratory distress syndrome (ARDS), can result from a variety of initial insults. In both of these forms of lung injury, inflammation is present in the lungs. With inflammation, pulmonary vascular permeability increases and liquid leaks out of the blood vessels. The liquid carries plasma proteins with it. When enough liquid escapes from the vessels, liquid begins to enter the alveoli, a condition known as alveolar edema. Initially, discrete alveoli in the dependent (bottom portion of the) lung become flooded and are interspersed with alveoli that remain aerated. With disease progression, most alveoli in the dependent lung become flooded; in the nondependent lung, some alveoli become flooded and are interspersed with other alveoli that remain aerated. From the onset of edema, the additional liquid in the airspace effectively thickens the alveolar-capillary membrane across which oxygen and carbon dioxide must be exchanged, making respiration difficult. Further, in ALI/ARDS, lung compliance is reduced, which makes breathing difficult.

ALI/ARDS patients are treated by mechanical ventilation, which assists gas exchange and keeps patients alive but often causes an over-distension injury (ventilator-induced lung injury, VILI) which exacerbates the underlying lung disease and prevents patient recovery. It is now standard protocol to deliver a low tidal (breath) volume that has been shown to decrease mortality. However, mortality still exceeds 35%.

It has been hoped that administration of exogenous surfactant would reduce surface tension, increase lung compliance and protect against VILI. Thus, multiple randomized clinical trials have tested tracheal administration of exogenous surfactant in ALI/ARDS patients. However, exogenous surfactant administration has not altered clinical outcome.

In VILI, the site of over-distension injury is likely in aerated alveoli adjacent to liquid-flooded alveoli. In liquid-flooded alveoli, the air-liquid interface forms a concave meniscus. Due to surface tension at the meniscus and pressure drop across the meniscus, liquid flooded alveoli are shrunken and adjacent aerated alveoli are, due to interdependence, expanded. Further, with ventilation, the flooded and aerated alveoli exhibit normal and reduced compliance, respectively. This difference in expansion mechanics between adjacent aerated and liquid-flooded alveoli is responsible for the ventilation induced over-distension of aerated alveoli located adjacent to liquid-flooded alveoli.

Neonatal Respiratory Distress Syndrome (RDS).

Surfactant is produced during the third trimester of gestation. Premature babies born prior to surfactant production used not to survive. Since the 1980's, tracheal instillation of exogenous surfactant has enabled such premature babies to live. However, there remains room for improvement in the clinical treatment of neonatal RDS.

High Frequency Modes of Lung Treatment.

For various objectives such as loosening/clearance of airway mucus and improved mechanical ventilation, the lung has sometimes been subjected to percussion and to high frequency ventilation. Devices designed to implement such treatments, and the frequencies at which they operate, include: pneumatically and electrically powered processors; intrapulmonary percussive ventilation (1.7-5 Hz); flutter valve therapy; high-frequency chest wall oscillation (5-25 Hz); high frequency positive-pressure ventilation (1-1.8 Hz); high-frequency jet ventilation (510 Hz); high-frequency oscillatory ventilation (1-50 Hz); high-frequency flow interruption (515 Hz, where the flow interruption occurs during inspiration, not expiration); and high-frequency percussive ventilation (5.2 Hz). None of these 'high-frequency' treatments operate at a frequency greater than 50 Hz.

Active Deflation.

Certain existing modes of ventilation have incorporated active deflation. Although now out of use, ventilation with negative end-expiratory pressure (NEEP)—available on Puritan Bennett AP series and Bird Mark 7 and 8 ventilators—can use a Venturi tube to actively draw air out of the airways and lower the minimal tracheal pressure at end-expiration below atmospheric pressure. In a Venturi tube, a high pressure gas jet is forced through a small orifice at the tube end while there is a second port in the tube for entrance of a different gas at lower velocity. The jet accelerates the lower velocity gas by entrainment.

High-frequency oscillatory ventilation uses an oscillator to move a diaphragm at one end of a chamber. On its forward stroke the oscillator moves air into the lungs; on its backward stroke it actively pulls air out of the lungs. During the backward stroke/expiration, tracheal pressure becomes negative. HFOV is most frequently used in neonatal ventilation, although it is used in adults as well.

SUMMARY OF THE INVENTION

In one aspect of the present invention, a surface tension lowering agent is added to alveolar edema liquid to (i) directly lessen over-distension injury of air-filled alveoli located adjacent to liquid-filled alveoli, and (ii) promote equitable edema liquid redistribution among alveoli. Such surface tension lowering agents may include certain rhodamine dyes.

In another aspect of the present invention, an active, accelerated deflation method is applied during mechanical ventilation of the edematous lung to promote equitable edema liquid redistribution between alveoli. An embodiment of the present invention includes an apparatus for generating such pressure waveforms.

In yet another aspect of the present invention, high frequency vibration of, or step or impulse force application to, the edematous lung promotes equitable edema liquid redistribution among alveoli. Such vibrations, or step or impulse forces, may be applied by various means.

BRIEF DESCRIPTION OF THE DRAWINGS

For a more complete understanding of the present invention, reference is made to the following detailed description of exemplary embodiments considered in conjunction with the accompanying drawings, in which:

FIGS. 4A and 4B are a pair of enhanced micrographs showing a local alveolar edema model and a global permeability edema model in experiments performed to demonstrate an embodiment of the present invention;

FIG. 5 is a bar chart comparing the effects of dye inclusion in edema liquid on surface tension at two alveolar pressures in experiments performed to demonstrate an embodiment of the present invention;

FIGS. 12A and 12B are a pair of schematic images generated by a computational fluid dynamics model, representing the effect of vibrating a liquid-filled alveolus according to an embodiment of the present invention;

FIGS. 12C, 12D, and 12E are a group of schematic drawings illustrating a conceptual model of the effect of vibration on edematous alveolar surface tension, performed according to an embodiment of the present invention, on edematous alveolar surface tension;

DETAILED DESCRIPTION OF THE INVENTION

Figure 1:
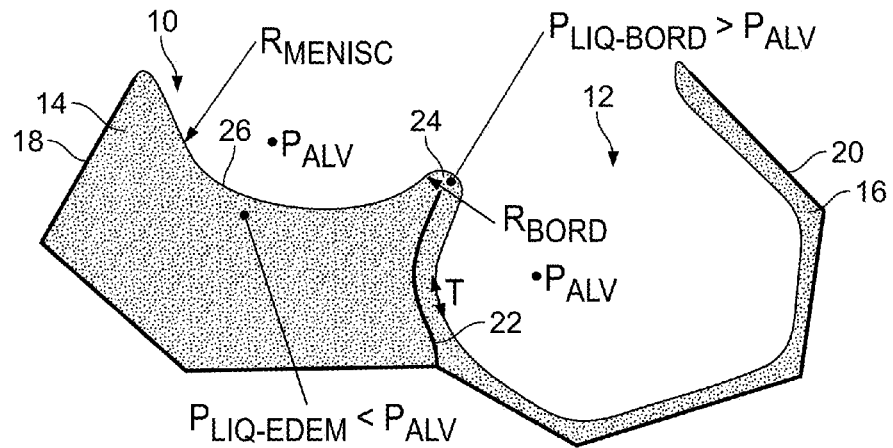
FIG. 1 is a schematic illustration of a novel analysis of regional liquid phase pressures in a liquid-filled alveolus adjacent to an air-filled alveolus, made according to an embodiment of the present invention.

FIG. 1 is a schematic drawing of regional liquid-phase pressures in a liquid-filled (i.e., edematous) alveolus 10 adjacent to an air-filled alveolus 12, according to a novel analysis of the mechanics of alveolar edema by the inventor of the present invention. The shaded areas 14, 16 represent liquid. The dark lines represent alveolar wall 18, 20, 22, where alveolar wall 22 is also a septum 22 between the liquid-filled alveolus 10 and the air-filled alveolus 12. As the liquid lining layer is continuous between alveoli, such as alveoli 10, 12, the edema liquid 14 of the liquid-filled alveolus 10 is continuous with the liquid lining layer 16 of the air-filled alveolus 12. By Law of Laplace, $P_{ALV} > P_{LIQ\text{-}EDEM}$, where $P_{ALV}$ is transpulmonary pressure and $P_{LIQ\text{-}EDEM}$ is liquid pressure in the edematous alveolus, and the difference between the two pressures is proportional to surface tension T. Thus, pressure is greater in the air-filled alveolus 12 than in the liquid-filled alveolus 10. Due to pressure imbalance, the septum 22 between the two alveoli 10, 12 bows into the liquid-filled alveolus 10 causing that alveolus 10 to shrink and the air-filled alveolus 12 to be expanded. Further, $P_{LIQ\text{-}BORD} > P_{ALV}$, where $P_{LIQ\text{-}BORD}$ is liquid pressure at the border 24 between the liquid-filled and air-filled alveoli 10, 12. Thus $P_{LIQ\text{-}BORD} > P_{LIQ\text{-}EDEM}$, forming a pressure barrier to liquid flow out of the edematous alveolus 10. The magnitude of the pressure barrier, $\Delta P_{BARRIER} = P_{LIQ\text{-}BORD} - P_{LIQ\text{-}EDEM}$, is determined by the Laplace relation and is proportional to the interfacial surface tension, T.

Figure 2A:
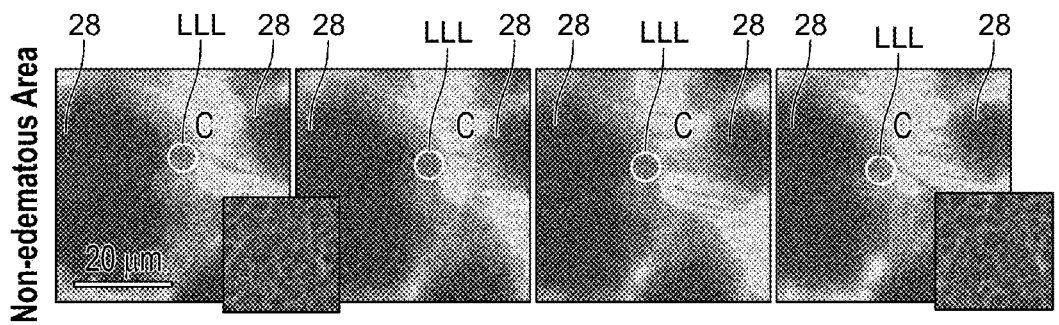
FIG. 2A is series of microphotographs showing a non-edematous control area of a lung where a liquid has been microinjected periodically into a group of surface alveoli to avoid persistence of alveolar flooding in an experiment performed to demonstrate an embodiment of the present invention.
Figure 2B:
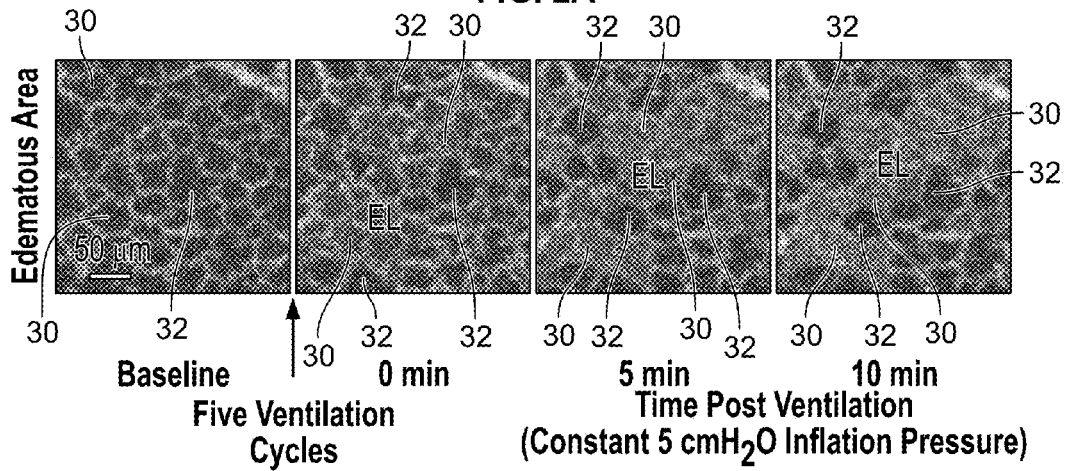
FIG. 2B is a series of microphotographs showing an edematous, experimental area of a lung where a liquid has been continuously delivered into group of surface alveoli to generate a local model of alveolar edema, in an experiment performed to demonstrate an embodiment of the present invention.
Figure 2C:
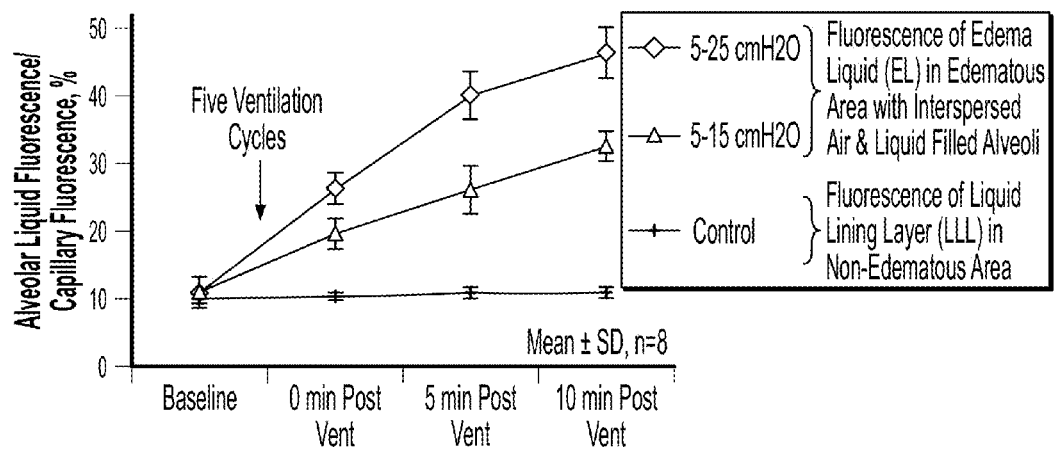
FIG. 2C is a graph showing grouped fluorescence-level data indicative of ventilation-induced injury for two different sets of ventilation pressure limits in an experiment performed to demonstrate an embodiment of the present invention.

Further, the degree of over-expansion of the air-filled alveolus is injurious. FIGS. 2A-2C demonstrate that in the presence of interspersed air- and liquid-filled alveoli, ventilation causes sustained injury (i.e., VILI) to the alveolar-capillary membrane.

Referring to FIGS. 2A and 2B, a local edema model was generated in the isolated, perfused rat lung. Fluorescein (34 µM) was included in the perfusate to label the capillaries (C). Non-fluorescent normal saline with 5% albumin was microinjected into a group of surface alveoli and the area was imaged by confocal microscopy at $P_{ALV}$ of 5 cmH$_2$O. The lung was ventilated five times between $P_{ALV}$ of 5 and 25 cmH$_2$O and then returned to a constant $P_{ALV}$ of 5 cmH$_2$O for 10 min of additional imaging. The five ventilation breaths generated an over-distension injury in areas of interspersed air- and liquid-filled alveoli, as evidenced by fluorescein escape from the vasculature and entrance into the alveolar liquid, that persisted even after the lung was returned to a constant, low volume.

The micrographs of FIG. 2A show a control area of a rat lung in which microinjections were delivered periodically, such that liquid cleared from alveoli between injections and the area did not become edematous. White circles label an area of the alveolar liquid lining layer (LLL) and insets show a lower magnification of the alveolar field. The micrographs of FIG. 2B show an area in which microinjections were delivered continuously such that some alveoli remained liquid-filled (visible, e.g., as gray areas 30 in the post-ventilation images) and a local alveolar edema model was established. Exemplary air-filled alveoli are shown as dark areas 32. In the baseline (left-most) image of the edematous area, liquid-filled alveoli 30 are not detectable as the edema liquid was not fluorescent. Post ventilation, LLL fluorescence remained unchanged in the non-edematous area but edema liquid (EL) fluorescence increased in the edematous area. Further, over the 10 min of imaging post injection with the lung held at constant, low inflation volume, EL fluorescence increased progressively, indicating the injury was not transient, but sustained.

FIG. 2C is a graph, showing grouped data for the tests described with relation to FIGS. 2A and 2B for two different sets of ventilation pressure limits, demonstrating that the means of detecting VILI discussed above is sensitive to the degree of injury resulting from the mechanical ventilation of the lung.

As lung ventilation in the presence of discrete alveolar flooding injures alveoli remaining air-filled in a surface tension-dependent fashion, surface tension reduction would directly lessen over-distension injury and equitable redistribution of the edema liquid among alveoli would, by equalizing forces across septa between alveoli, indirectly protect against over-distension injury. To promote equitable edema liquid distribution, the cause of liquid trapping in discrete alveoli must be understood. Liquid-filled alveoli are generally stable, but occasionally clear.

Figure 3:
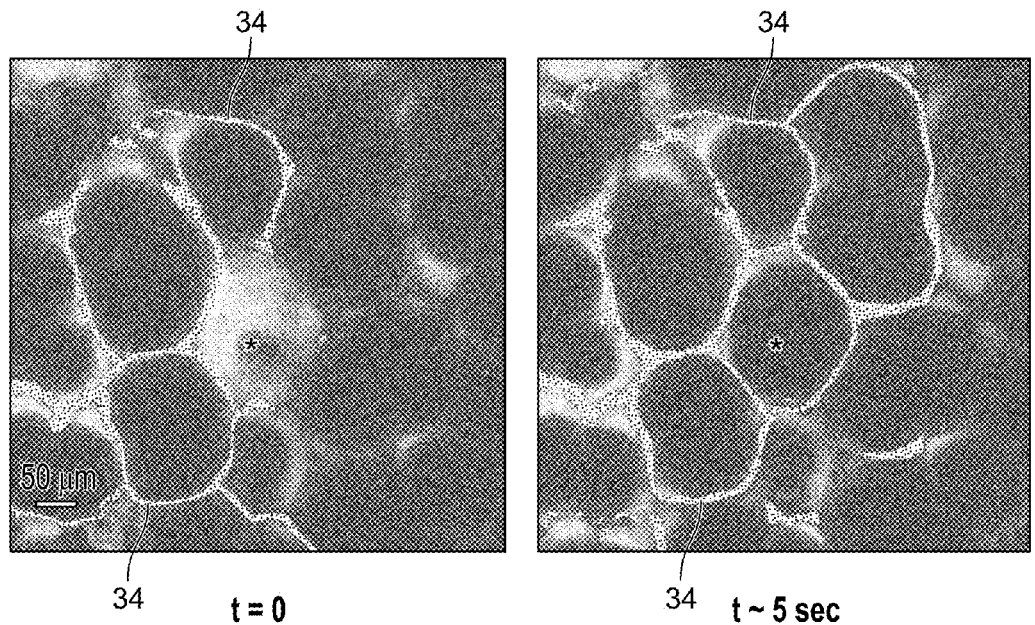
FIG. 3 is a pair of micrographs depicting a liquid-filled alveolus that has spontaneously cleared.

When liquid-filled alveoli clear, they do so spontaneously, unpredictably and instantaneously; the liquid disperses amongst neighboring alveoli. That is, the liquid from alveoli that "clear" is in fact equitably redistributed amongst surrounding alveoli. Referring to FIG. 3, a pair of micrographs depict the spontaneous clearing of a liquid-filled alveolus, indicated by an asterisk (*). The micrographs are sequential optical sections from a z-stack of images, with a time of about 5 sec between images. In between imaging the two sections, the liquid cleared from the (*) alveolus, leaving it air-filled. Liquid-filled alveoli are occasionally seen to clear spontaneously. Liquid clearance is instantaneous. Alveoli "pop" open as liquid disperses to nearby alveoli. In FIG. 3, the lightly-stippled areas 34 represent liquid in or adjacent to alveolar walls.

The stability of liquid-filled alveoli can be understood with the novel analysis of the spatial variation in liquid phase pressure, $P_{LIQ}$, of the edematous alveolus 10 discussed above with respect to FIG. 1. The analysis demonstrates that ventilation over-distends aerated alveoli located adjacent to liquid-filled alveoli to a degree that is proportional to surface tension and there is a pressure barrier $\Delta P_{BARRIER}$—equal to $P_{LIQ\text{-}BORD}$ at the border between two alveoli minus $P_{LIQ\text{-}EDEM}$ within the edematous alveolus—that opposes the escape of edema liquid from discrete flooded alveoli. Further, $\Delta P_{BARRIER}$ is proportional to the interfacial surface tension. To protect against ventilator-induced lung injury, the various aspects of the present invention provide approaches to reduce alveolar over-distension both directly, by lowering surface tension, and indirectly, by overcoming $\Delta P_{BARRIER}$ to equalize edema liquid distribution among alveoli. Such approaches include, but are not necessarily limited to:

1. Surface tension reduction, which includes combining an additive with instilled exogenous surfactant to reduce surface tension, thus directly reducing over-distension injury and also lowering the pressure barrier to promote equitable edema liquid distribution among alveoli;
2. Active deflation during mechanical ventilation, which includes the use of active, accelerated deflation in combination with maintenance of a positive end-expiratory pressure (PEEP) to transiently increase $P_{LIQ\text{-}EDEM}$ and reduce the pressure barrier; and
3. Vibration or step or impulse force application to the lung, which includes vibrating the lung or applying a step or impulse force to the lung to impose spatial variation in surface tension and/or to perturb the normal pressure gradient in the edematous alveolar liquid, and, in a random fashion, increase the likelihood of overcoming the pressure barrier to cause edematous alveolar clearance.

1. Surface Tension Reduction

Additives to alveolar edema liquid were tested in the rat lung model for their ability to reduce surface tension. FIGS. 4A and 4B are a pair of micrographs showing alveolar edema models. The model of FIG. 4A is a local model generated by alveolar microinfusion of 5% albumin solution labeled with 2',7'-bis-(2-carboxyethyl)-5- (and -6)-carboxyfluorescein (BCECF). The model of FIG. 4B is a global permeability edema model, generated by inclusion of 6 mM oleic acid in lung perfusate, plus 34 µM fluorescein also in the perfusate for visualization. As shown by comparison of FIGS. 4A and 4B, either method generates the characteristic pattern of interspersed air- and liquid-filled alveoli. Light and medium gray areas, such as areas 36, indicate the presence of liquid. Darker areas, such as areas 38, indicate air-filled alveoli.

In the alveolar edema model, and referring back to FIG. 1, $P_{LIQ\text{-}EDEM}$ is measured with a servo-nulling system; alveolar air pressure, $P_{ALV}$, is measured with a transducer at the trachea of the statically inflated lung; and the interfacial radius of curvature, $R_{MENISC}$, is determined by capturing the edematous alveolar meniscus in a z-stack of confocal images. Surface tension, T, is determined from the Laplace relation: $P_{ALV}-P_{LIQ\text{-}EDEM}=2\ T/R_{MENISC}$. Surface tension, T, is determined under control conditions and with additives included in the edema liquid, to determine the additives' abilities to lower surface tension. As discussed below with respect to FIGS. 5, 6A, 6B, 7A, 7B, 7C, 7D, 8A, and 8B, at high lung volume the dyes BCECF (32 μM), fluorescein (17 μM), calcein AM (20 μM) and sulforhodamine G (1 μM) do not alter surface tension whereas the dyes rhodamine WT (RWT, 1 μM) and sulforhodamine B (1 μM) decrease surface tension by 30%.

FIG. 5 is a bar chart comparing the effects of dye inclusion in edema liquid on surface tension at $P_{ALV}$ of 5 and 15 cmH$_2$O. All measurements were made in alveoli filled with 5% albumin in normal saline and following two ventilation cycles between 5 and 15 cmH$_2$O. Statistics were assessed only between groups with at least n=3 replicates and are reported as mean+/−SE. In the absence of dye (control), laser intensity and gain of the confocal microscope (Leica SP5) were elevated to visualize the edematous alveolar meniscus, and thus determine its radius and calculate surface tension. At $P_{ALV}$=5 cmH$_2$O, the dye BCECF increased surface tension above control (*). No other dye altered surface tension. At $P_{ALV}$=15 cmH$_2$O, rhodamine WT decreased surface tension by 30% compared with all other groups of at least n=3 replicates (‡). Comparisons were not made to groups of n=2 replicates. Inflation from $P_{ALV}$ of 5 to 15 cmH$_2$O caused a significant increase in surface tension (#).

Figure 6A:
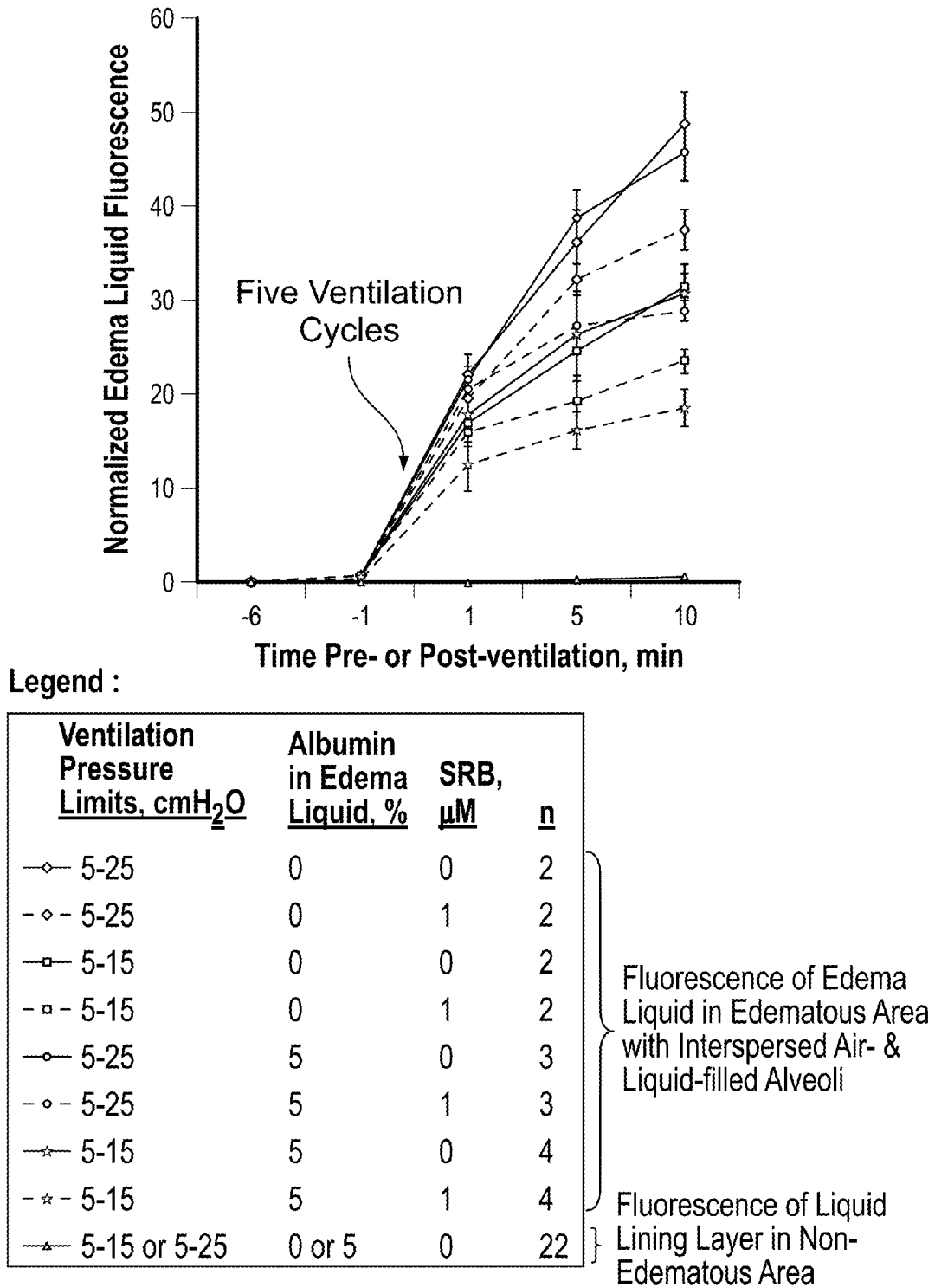
FIG. 6A is a graph of edema liquid fluorescence against pre- and post-ventilation time in the absence or presence of bovine serum albumin and the absence or presence of sulforhodamine B (SRB) in experiments performed to demonstrate an embodiment of the present invention.
Figure 6B:
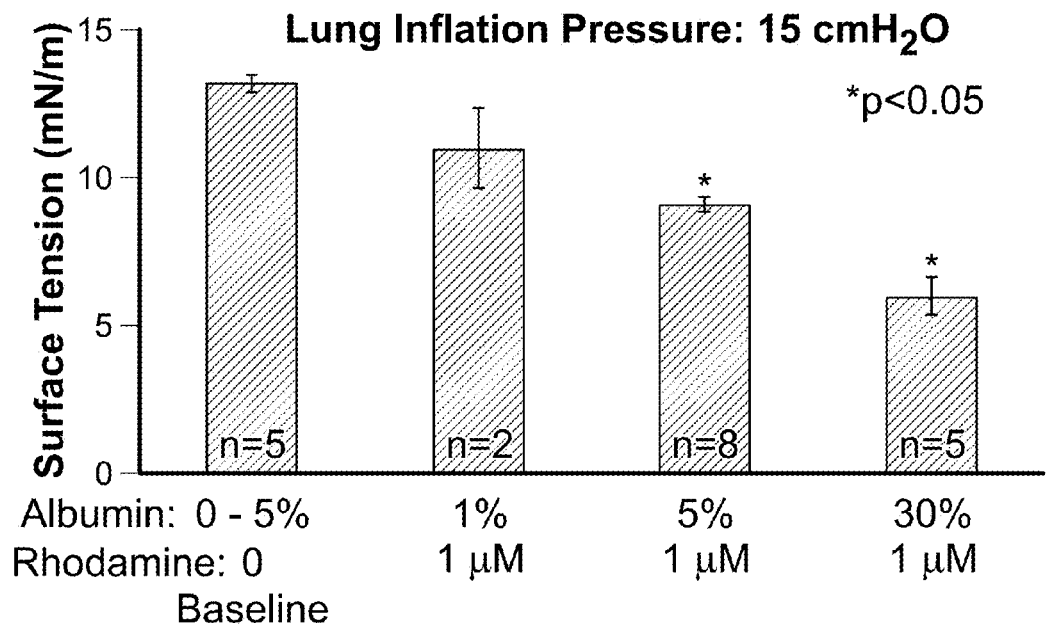
FIG. 6B is a bar chart of alveolar surface tension in the presence of a dye and varying amounts of albumin in experiments performed to demonstrate an embodiment of the present invention.

FIGS. 6A and 6B demonstrate that SRB and RWT reduce lung injury by reducing surface tension, and that both additive dyes are more effective when combined with albumin. FIG. 6A shows data from same injury model as discussed with respect to FIGS. 2A, 2B, and 2C with alveolar liquid fluorescence levels normalized by capillary fluorescence levels and adjusted to zero at baseline. A local edema model was generated with Ringer's solution+5% dextran (no albumin) or with normal saline+5% albumin. In the absence of SRB, albumin inclusion does not affect degree of injury. SRB inclusion reduces injury, more effectively in the presence than in the absence of albumin. FIG. 6B shows that SRB/RWT lower surface tension more effectively in the presence of greater concentrations of albumin. FIG. 6B presents combined data from the two dyes, although the dyes themselves were not combined in any experiment. It may be noted that 30% albumin, which was tested and reported in FIG. 6B, is not a physiologic condition.

Figure 7A:
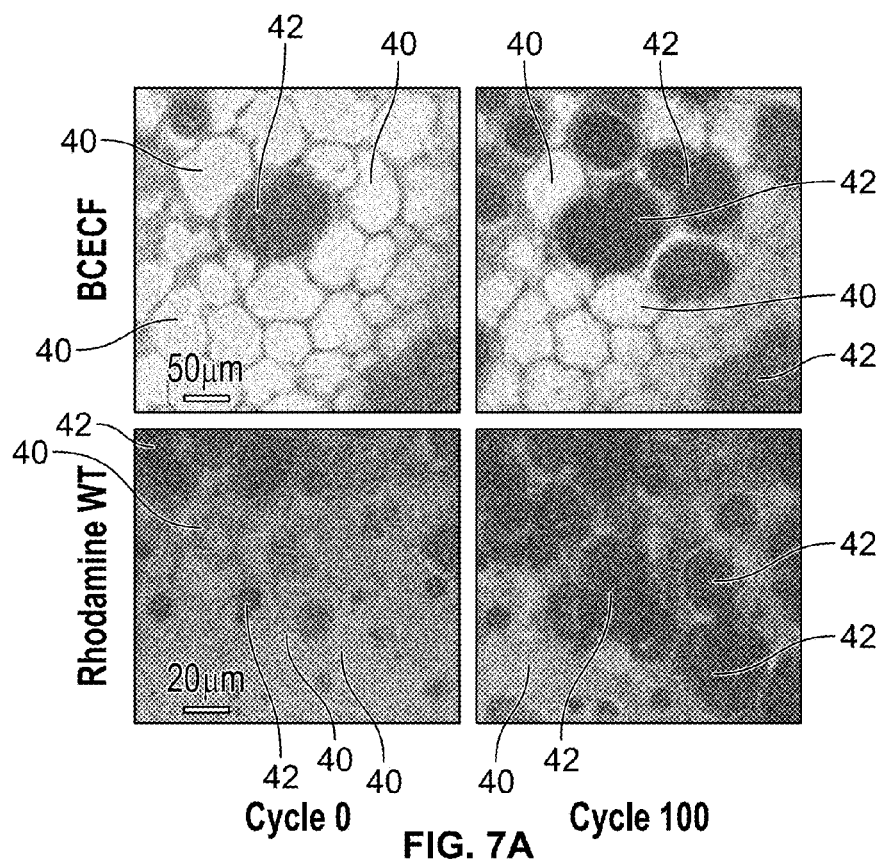
FIGS. 7A and 7B are a pairing of a set of micrographs and a graph comparing clearance of alveoli in a local edema model in the presence of either of two dyes, in experiments performed to demonstrate an embodiment of the present invention.
Figure 7B:
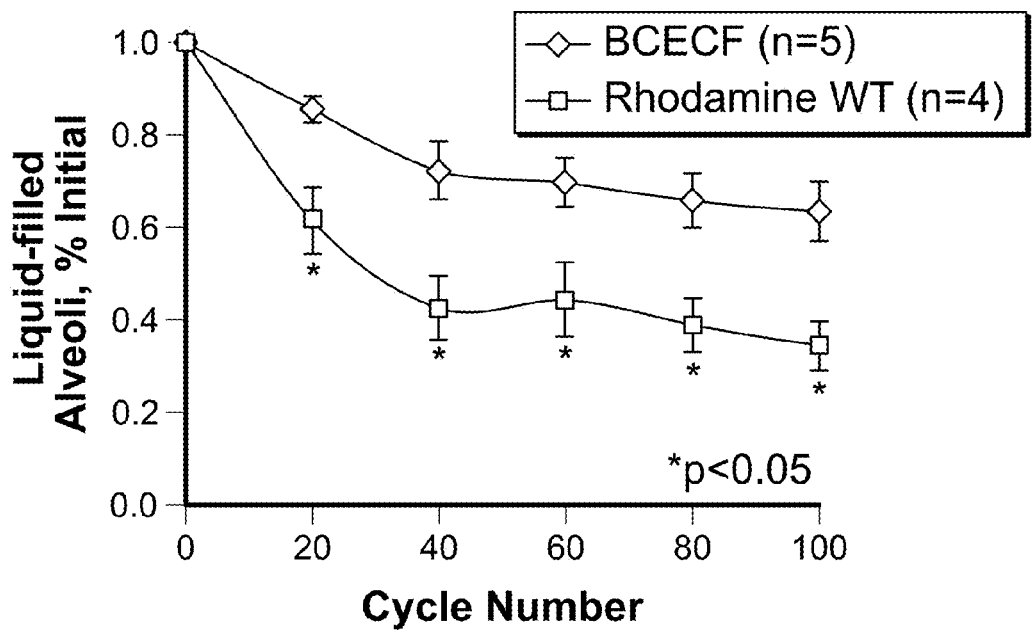
Figure 7C:
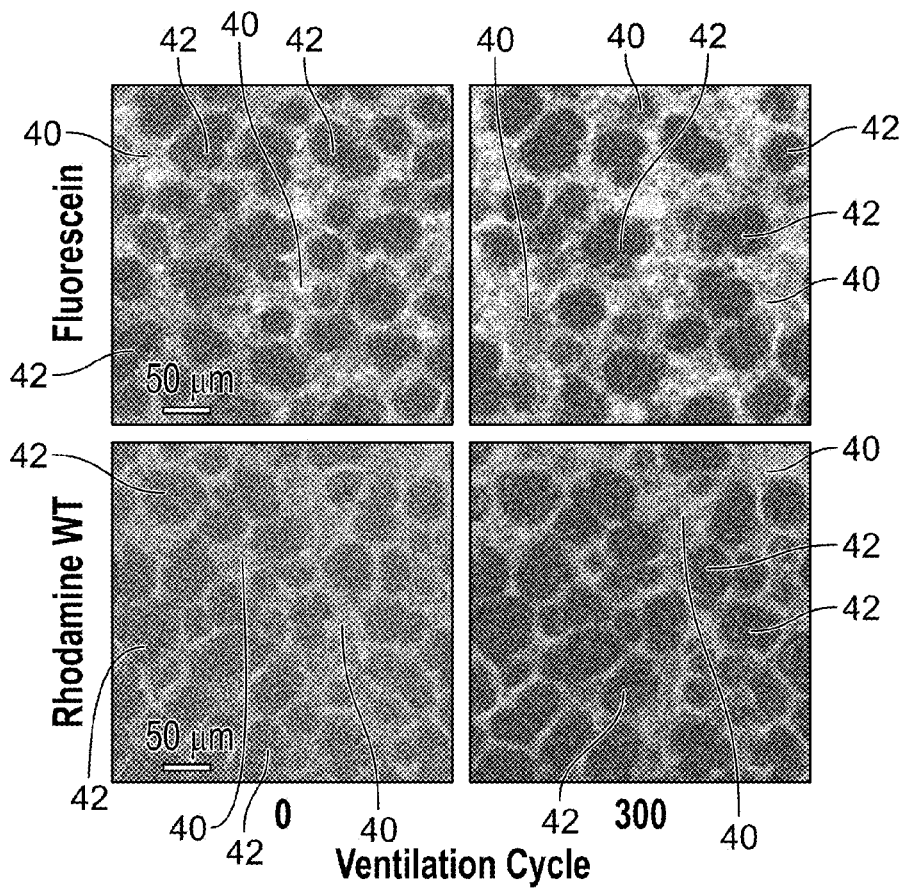
FIGS. 7C and 7D are a pairing of a set of micrographs and a graph comparing clearance of alveoli in a global permeability edema model in the presence of the dyes in experiments performed to demonstrate an embodiment of the present invention.
Figure 7D:
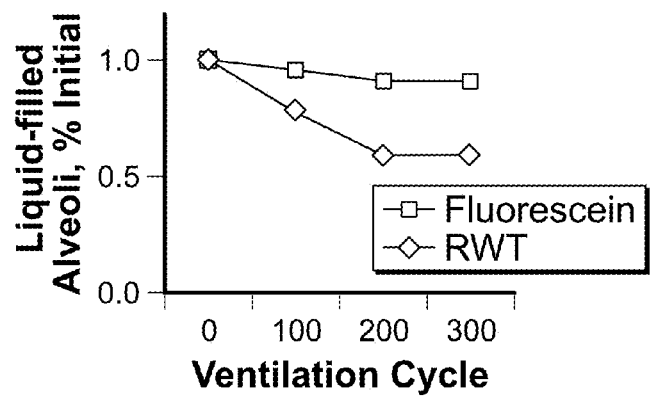

FIGS. 7A, 7B, 7C, and 7D show that greater alveolar liquid clearance is achieved with rhodamine WT than with BCECF. The micrographs of FIG. 7A show the change in a local edema model created with inclusion of BCECF (32 uM) or rhodamine WT (1 uM) in the edema liquid. The edematous area was imaged before and after 100 cycles of sinusoidal ventilation between $P_{ALV}$ of 5 and 15 cmH$_2$O, at 0.2 Hz The graph of FIG. 7B shows the effect of multiple ventilation cycles on edematous alveolar clearance. The micrographs and graph of FIGS. 7C and 7D show the results of the same experiment replicated in a global permeability edema model with inclusion of fluorescein (36 μM) or RWT (2 μM) in the perfusate. In all micrographs of FIGS. 7A and 7C, exemplary liquid-filled alveoli 40 are shown as a lighter gray than air-filled alveoli 42.

Figure 8A:
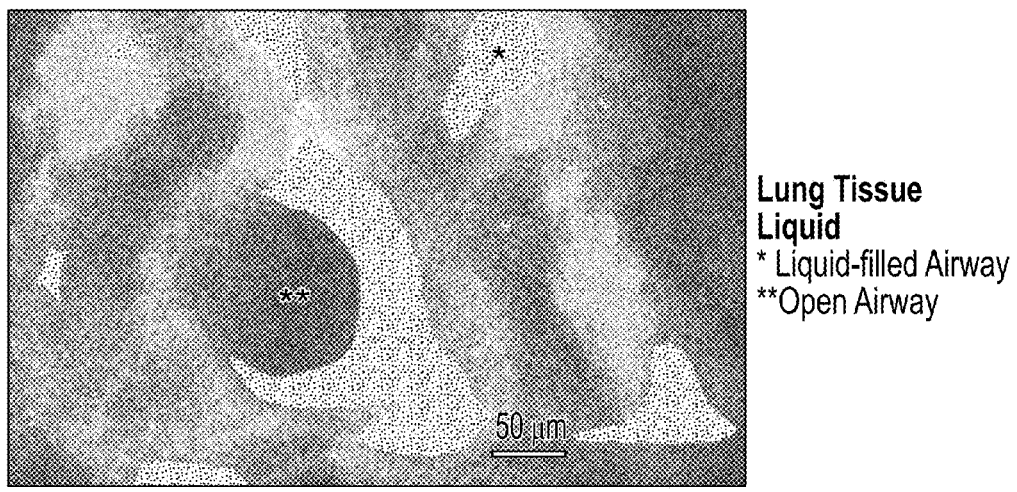
FIGS. 8A and 8B are a pairing of an enhanced micrograph and a graph depicting inflation of immature fetal rat lung lacking native surfactant in experiments performed to demonstrate an embodiment of the present invention.
Figure 8B:
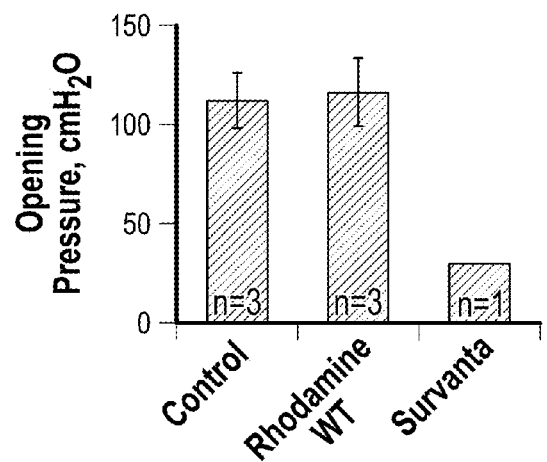

FIGS. 8A and 8B are a pairing of an enhanced micrograph and a graph depicting inflation of immature (embryonic day 18) fetal rat lung lacking native surfactant. The micrograph is a confocal image of the inflated fetal lung. Air is shown in dark gray, epithelial cells are shown in light gray, and airway liquid is shown with light stippling. Liquid was instilled in the trachea prior to inflation. FIG. 8B presents the pressures at which the alveoli opened under controlled conditions in the presence of each of two additives.

The additive experiments discussed above with respect to FIGS. FIGS. 5, 6A, 6B, 7A, 7B, 7C, 7D, 8A, and 8B demonstrate that SRB has the ability to lessen direct ventilation-induced over-distension injury and that the protection is enhanced by the presence of albumin in the edema liquid (see FIGS. 6A and 6B). For a constant rhodamine concentration, addition of albumin lowers surface tension in a dose-dependent manner. Thus, SRB/RWT are expected to be most beneficial to patients with the most severe lung injury, in whom albumin concentration in the edema liquid is greatest. Further, the abilities of SRB and RWT to promote edematous alveolar clearance were tested. Edema was generated with either BCECF or RWT included in the edema liquid (local edema model) or with fluorescein or RTW included in the perfusate (global edema model). More alveoli were found to clear after ventilation when RWT was present than when either BCECF or fluorescein were present (see FIG. 5). Given that SRB lowers surface tension to the same degree as RWT (see FIG. 5) and provides direct protection against over-distension injury (see FIG. 6A), SRB is likewise expected to promote alveolar clearance to the same degree as RWT.

Without being bound by theory, it is believed that SRB and RWT, incorporated into alveolar edema liquid of the lung as in embodiments of the present invention, lower surface tension not directly but rather by promoting interfacial adsorption of surfactant that is natively present in the lung in situ, and in the isolated, perfused lung. It is further believed that SRB or RWT combine with albumin, thus further promoting surfactant adsorption. To rule out direct surface activity of SRB/RWT, the inventor used a fetal rat lung model lacking surfactant (see FIGS. 8A and 8B). The pressure required initially to inflate the completely liquid-filled fetal lung is proportional to the surface tension of the liquid. Tracheal instillation of exogenous surfactant (e.g., Survanta) lowers the opening pressure, as well as subsequent ventilation pressures. Instillation of RWT alone, without surfactant, failed to decrease opening pressure, thus confirming that RWT is not directly surface active.

SRB/RWT Chemistry

SRB and RWT have a surface tension lowering capability that the dyes fluorescein, BCECF, calcein red-orange AM, and even sulforhodamine G lack. SRB and RWT also have a unique aspect to their chemical structure. While all six of the above dyes are aromatic fluorescent compounds, and all but calcein red-orange AM comprise anionic groups, SRB and RWT are distinguished by the additional presence of an iminium cation ($R_1=N^+-R_2R_3$). It would thus be expected that other molecules with structures similar to that of SRB and RWT would likewise promote surfactant adsorption and reduce surface tension when instilled into the lung according to embodiments of the present invention. Aromatic dissociated salt anions possessing one or more carboxyl, hydroxyl, or equivalent groups plus one or more cationic groups may also act equivalently to SRB and RWT. Additives other than aromatic salts (e.g., zwitterionic salts) may also be effective in reducing surface tension when instilled into the lung.

In clinical applications of embodiments of the present invention, the surface tension-lowering additive could be mixed with exogenous surfactant and instilled in the trachea. The patient would then be ventilated and the instilled surfactant would act as a delivery vehicle, transporting the additive to alveoli, where it would act to lower surface tension. It is possible that additives could be effectively instilled in the trachea in the absence of exogenous surfactant, or instilled in a more distal airway (e.g., by bronchoscope) in the presence or absence of exogenous surfactants. It is also possible that an additive could be administered intravenously, and make its way into the lungs as a result of the increased vascular permeability that is a component of ALI/ARDS.

Neonatal Respiratory Distress Syndrome.

A surface tension-lowering additive has potential application in the treatment neonatal RDS. Babies born prematurely before producing their own surfactant are treated by tracheal instillation of exogenous surfactant. Combining a surface tension lowering additive with the exogenous surfactant would increase the efficacy of the exogenous surfactant and/or lower surface tension more than exogenous surfactant alone. As a result, the neonatal lung could be initially inflated, and subsequently ventilated, with lower pressures than if surfactant alone were instilled. Instillation of a surface tension lowering additive in conjunction with exogenous surfactant should better protect the neonatal lung from injury than instillation of surfactant alone. Further, use of a surface tension lowering additive could lower the cost of treating neonatal RDS by decreasing the required exogenous surfactant dosage. In babies delivered just as they are beginning to produce native surfactant, SRB, RWT or equivalent might act as a bridge support, enhancing the activity of the initial, low levels of surfactant until more surfactant were produced.

Industrial Use of Additives.

By extension, additives such as those discussed above may be combined with industrial surfactants to enhance surfactant adsorption and surface tension reduction. Industrial surfactants are generally simpler in structure than pulmonary surfactant. Industrial surfactants are generally mono-molecular and may be positively charged, uncharged or negatively charged. With negatively charged surfactants, addition of RWT, SRB or equivalent would lower surface tension more than surfactant alone. With positively charged surfactants, a surface tension lowering additive could, for example, be the positive ion of a dissociated salt in combination with one or more negatively charged groups. The use of such an additive would lower surface tension more than surfactant alone.

2. Active Deflation During Mechanical Ventilation

According to embodiments of the present invention, sudden deflation of the lung will, effectively, catapult edema liquid out of the alveoli in which it is trapped. As discussed further herein, the effectiveness of this embodiment of the present invention has been demonstrated in the local alveolar edema model and global permeability edema model in the isolated, perfused rat lung.

Figure 9:
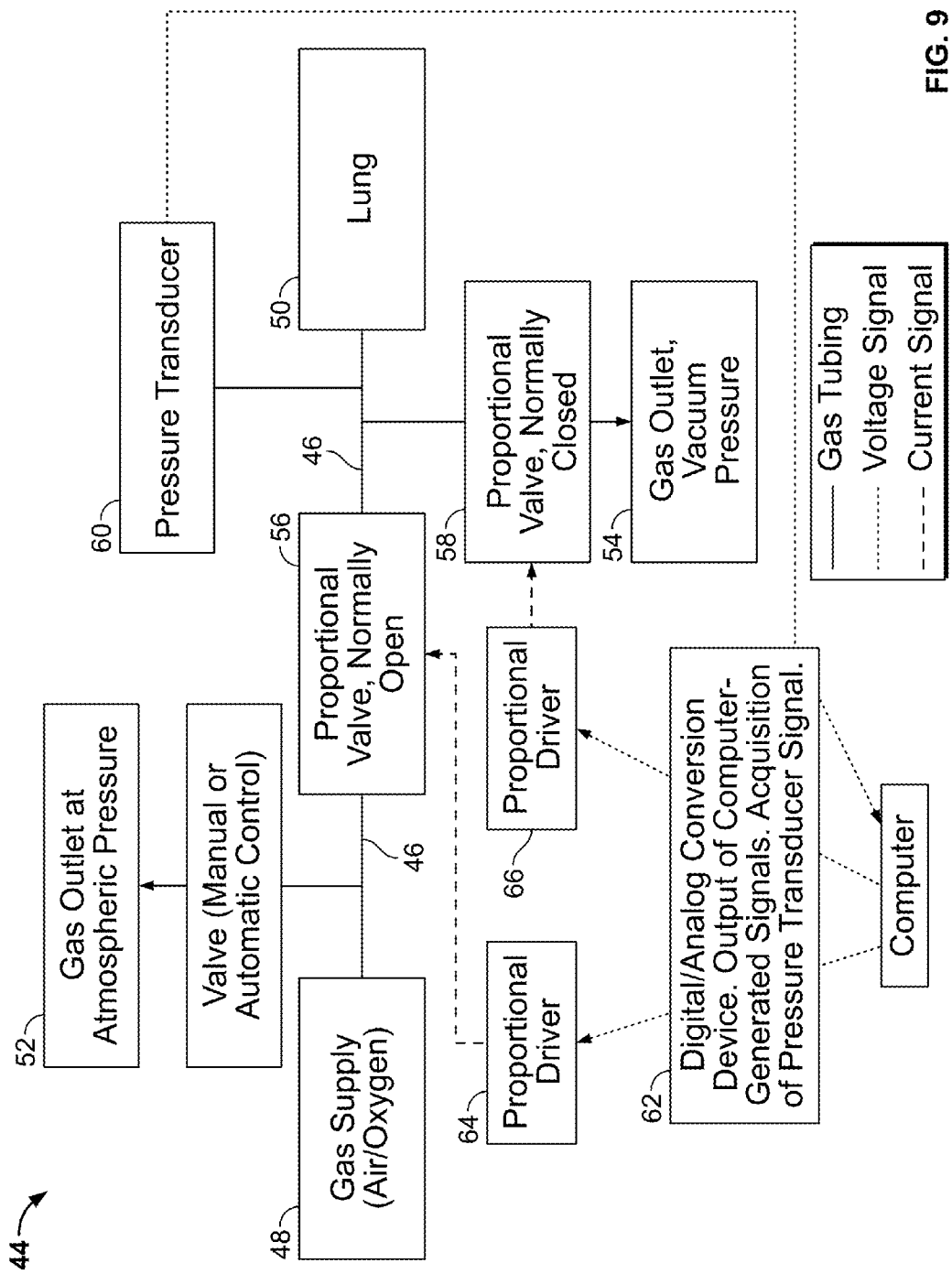
FIG. 9 is a schematic block diagram of an apparatus for the generation of custom ventilation pressure waveforms, according to an embodiment of the present invention.

FIG. 9 is a schematic block diagram of an apparatus 44 for the generation of custom ventilation pressure waveforms, according to an embodiment of the present invention. A tubing line 46 links the ventilation gas source 48 to the lung 50. Along the tubing line 46 are two outlets 52, 54, one outlet 52 opening to atmospheric pressure, the other outlet 54 opening to vacuum pressure. Located between the two outlets 52, 54 is a normally-open proportional valve 56, and along outlet 54 is a normally-closed proportional valve 58. Between outlet 54 and the lung 50, a pressure transducer 60 measures and indicates pressure in the tubing line 46. In some embodiments of the present invention, the pressure transducer 60 is proximate the end of the tubing line 46 where it is fluidly connected to the lung 50, such that the pressure measured by the pressure transducer 60 is substantially the same as the pressure at the entrance to the trachea (not shown). A custom Labview® program acquires pressure data from the transducer 60 and, in an open-loop fashion, provides voltage signals that control the proportional valves via a digital/analog conversion device 62 and appropriate proportional drivers 64, 66. The development of suitable computer programs and selection of conversion devices 62 and drivers 64, 66 are within the ability of those having ordinary skill in the relevant art. In some embodiments of the present invention, the first outlet 52 is omitted, and the normally-open proportional valve 56 is placed in the tubing line 46 between the end of the tubing line 46 that receives gas from the ventilation gas source 48 and the outlet 54.

In an embodiment of the present invention, the lung 50 is inflated to peak volume, and abrupt deflation is effected by simultaneous application of step voltage increases to valves 56, 58, causing the valves 56, 58 suddenly to close and open, respectively. Valve 58 remains open until the pressure measured in the tubing 46 has decreased to a targeted pressure, which may be the desired positive end-expiratory pressure, at which time voltage to valve 58 is returned to zero, causing valve 58 to close. At the subsequent, specified time for initiation of inflation, voltage to valve 56 is reduced exponentially such that valve 56 opens gradually and ventilation gas passes through valve 56 to inflate the lung 50. Thus, the lung 50 is actively deflated while maintaining a positive pressure at the lung 50. This maintenance of positive pressure at the lung 50 during mechanical deflation of the lung 50 is one of the characteristics of the present invention that distinguishes it over methods existing in the prior art.

The apparatus 44 of FIG. 9 is useful for generating a ventilation pressure waveform with gentle deflation (sinusoidal) when outlet 54 is open to the atmosphere and valve 58 is opened gradually during deflation, or with sudden, passive deflation (sawtooth) with an exponential increase in pressure and a sudden, passive decrease in pressure when outlet 54 is open to the atmosphere and valve 58 is opened suddenly at the start of deflation. When outlet 54 is attached to a vacuum source and valve 58 is opened suddenly at the start of deflation (accelerated sawtooth), as in embodiments of the present invention, the deceleration is sudden and accelerated.

Figure 10A:
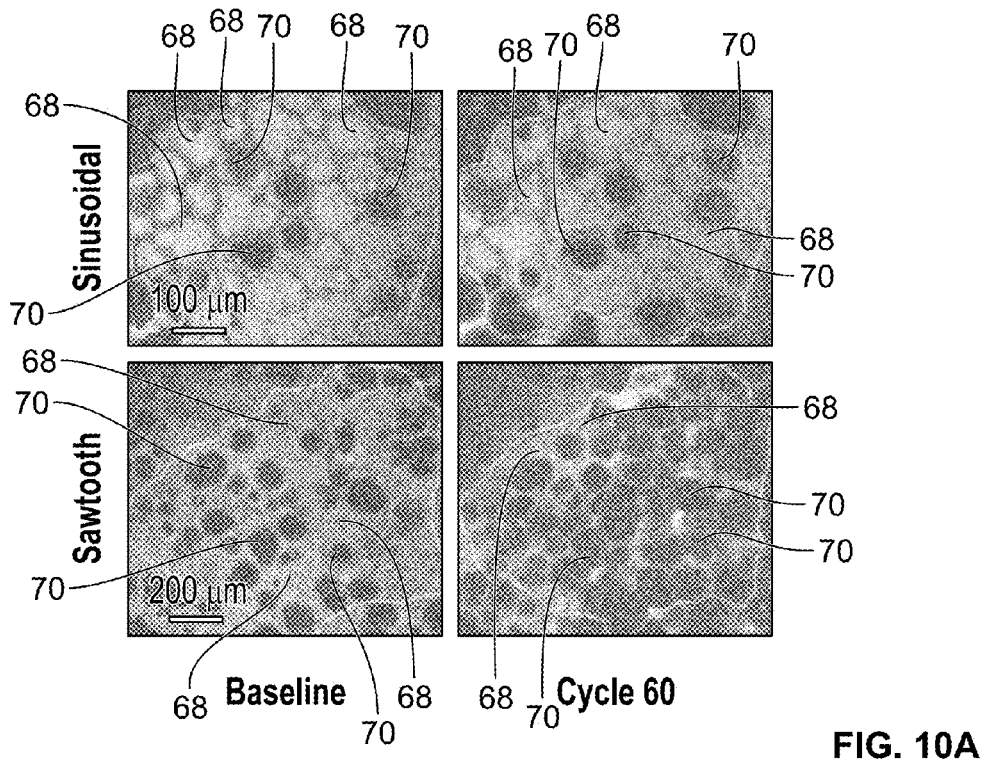
FIGS. 10A and 10B are a pairing of a set of micrographs and a graph comparing clearance of alveoli in a local edema model by ventilation using a sinusoidal pressure waveform and ventilation using a sawtooth waveform, according to embodiments of the present invention.
Figure 10B:
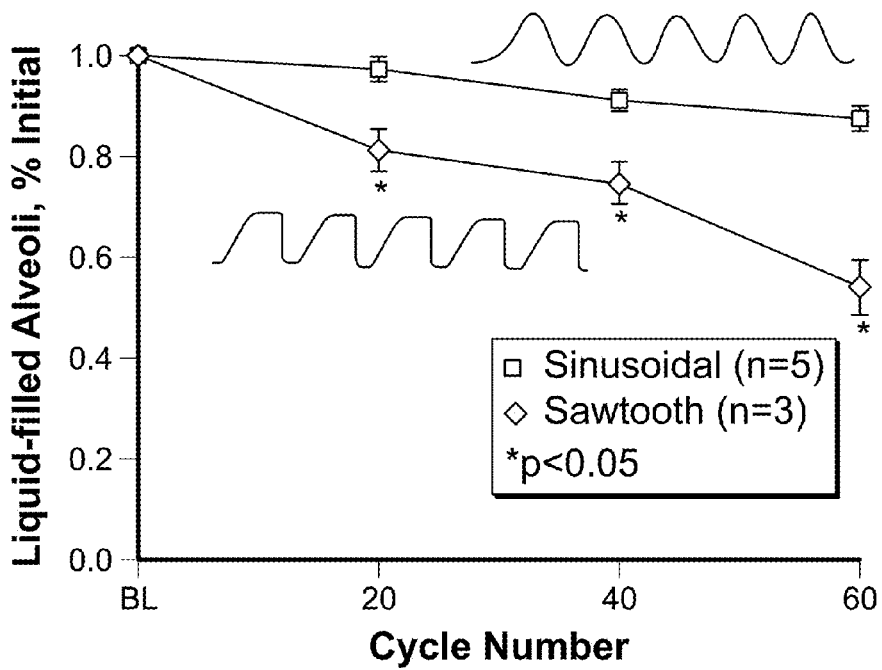
Figure 10C:
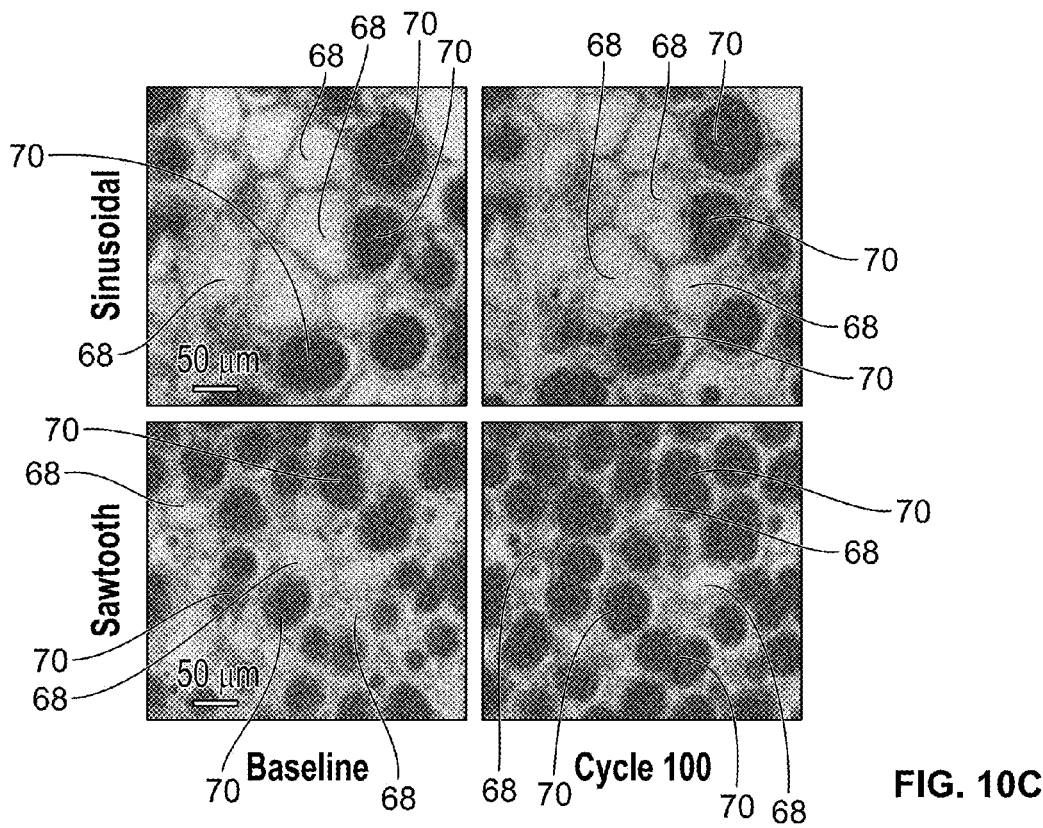
FIGS. 10C and 10D are a pairing of a set of micrographs and a graph comparing clearance of alveoli in a global permeability edema model by ventilation using a sinusoidal pressure waveform and ventilation using a sawtooth waveform, according to embodiments of the present invention.
Figure 10D:
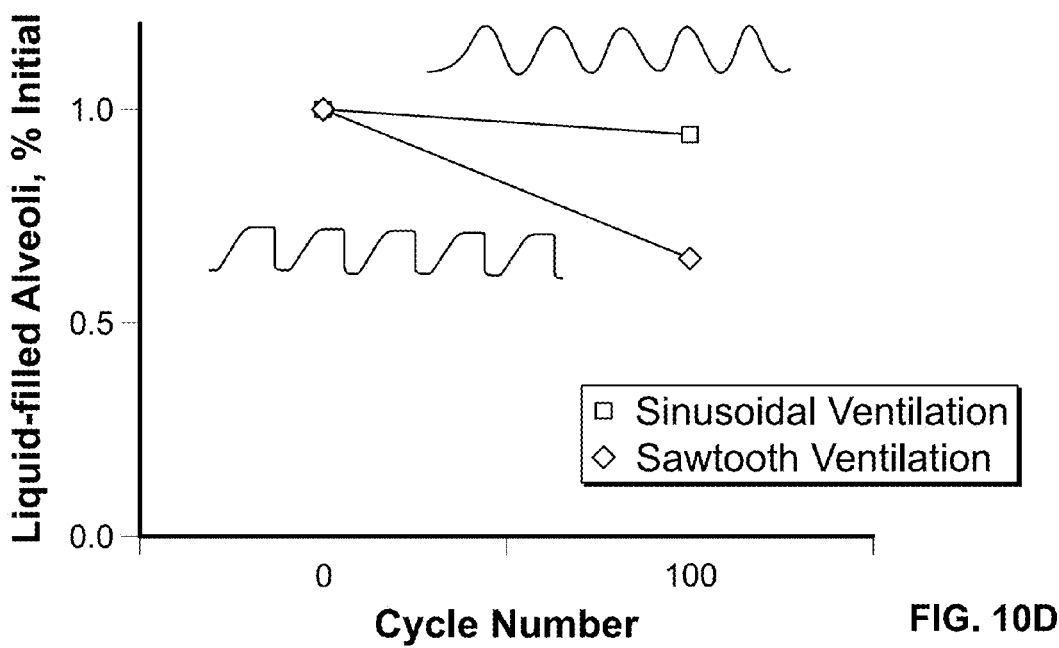

FIGS. 10A and 10B are a pairing of a set of micrographs and a graph comparing clearance of alveoli by ventilation using sinusoidal and sawtooth pressure waveforms, as are FIGS. 10C and 10D. FIGS. 10A and 10B illustrate results obtained ventilating a local edema model, and FIGS. 10C and 10D illustrate results obtained using a global permeability edema model. Both ventilation patterns were used at a cycle frequency of 0.2 Hz between $P_{ALV}$ of 5 and 15 cmH$_2$O. Baseline (BL), indicated on the graph of FIG. 10B, is following 20 cycles of sinusoidal ventilation in each group, to clear unstable alveoli and test the ventilation patterns on stably liquid-filled alveoli. As can be seen from the micrographs and graphs of FIGS. 10A, 10B, 10C, and 10D, ventilation using a sawtooth waveform opens a greater number of alveoli than does ventilation using a sinusoidal waveform, indicating that the abrupt deflation of the sawtooth ventilation clears alveolar liquid more effectively than sinusoidal ventilation. In FIGS. 10 A and 10C, exemplary liquid-filled alveoli 68 are indicated by lighter gray areas, and exemplary air-filled alveoli 70 are indicated by darker areas.

Figure 11:
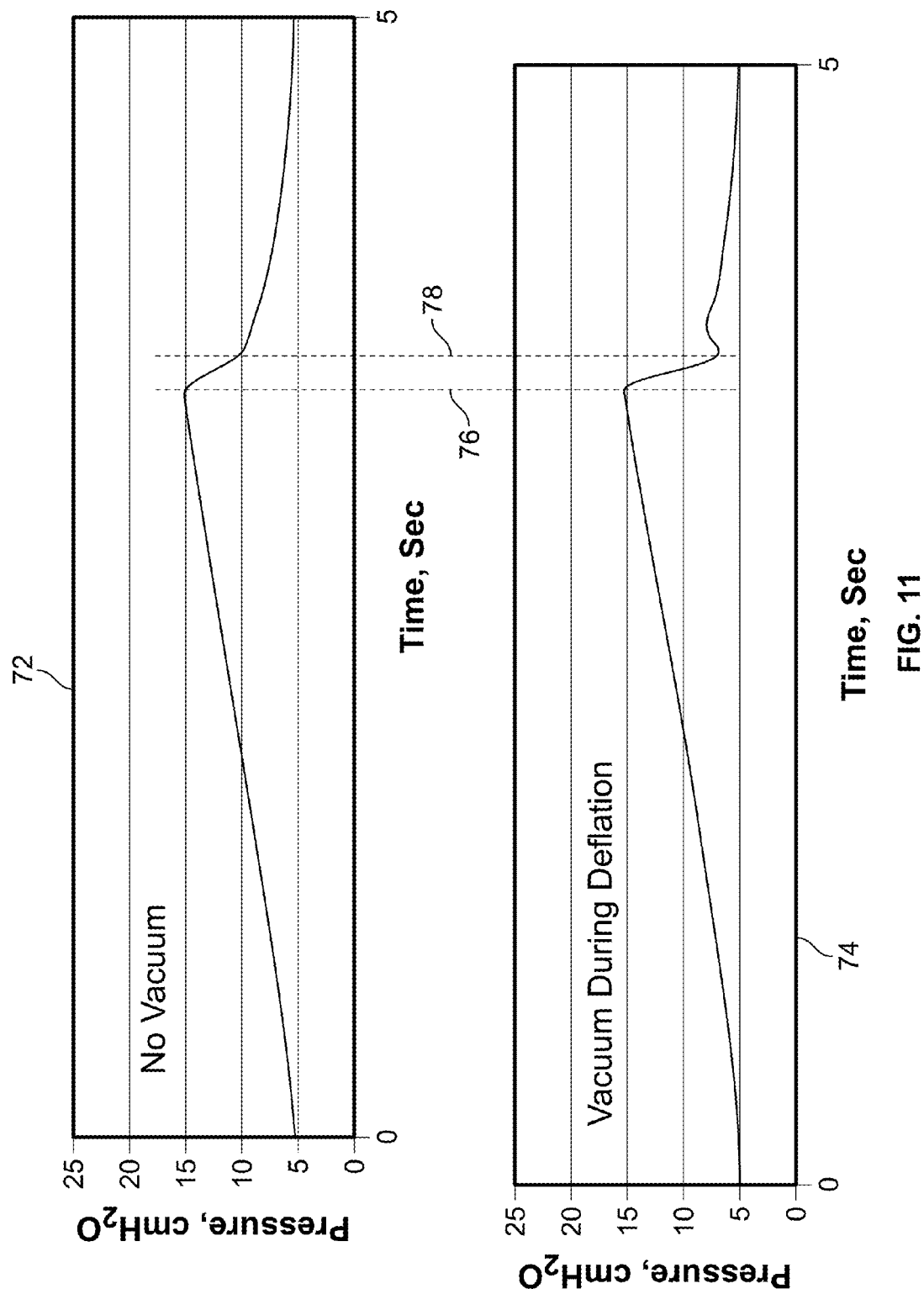
FIG. 11 is a pair of graphs showing the effect of vacuum acceleration during deflation on pressure ventilation waveforms generated according to embodiments of the present invention with the apparatus of FIG. 9.

In some embodiments of the present invention, the lung may be actively deflated at an accelerated rate (accelerated sawtooth), by applying vacuum pressure at gas outlet 54 of the ventilation apparatus 44 shown in FIG. 9 and opening valve 58 suddenly at the start of deflation. Results of this active deflation are shown in the graphs of FIG. 11. The upper graph 72 shows a waveform generated with atmospheric pressure at outlet 54 and sudden opening of valve 58 at the start of deflation. The lower graph 74 shows a waveform generated with vacuum pressure applied at outlet 54 and sudden opening of valve 58 at the start of deflation. The vertical lines lines 76, 78 indicate the time for the waveform of the upper graph (i.e., the waveform generated without vacuum) to decrease from 15 to 10 cmH$_2$O. As shown in the lower graph, application of vacuum at outlet #2 generates a waveform having a sharper deflation slope, with a shorter time required to decrease pressure from 15 to 10 cmH$_2$O. However, PEEP was maintained (i.e., tracheal pressure never decreased below a set, positive threshold value).

As discussed above with respect to FIGS. 9, 10A, 10B, 10C, 10D, and 11, faster deflation of the lung is effective in clearing liquid from alveoli. Such clearance may be achieved with one or a combination of the following methods, performed according to embodiments of the present invention:

1. Applying vacuum pressure at the exit of the ventilation tubing circuit (e.g., gas outlet 54 in the apparatus of FIG. 9) during deflation; and
2. Stimulating the abdominal and/or intercostal muscles, by functional electrical stimulation, or other means, to generate a cough-like motion synchronized with exhalation/deflation.

Either of the above two methods for causing active deflation, alone or in combination, could be combined with mechanical ventilation; non-invasive ventilation; or lung expansion devices including chest physiotherapy devices and high frequency oscillation devices.

Vacuum may be applied by known means such as vacuum pump, house vacuum line, Venturi tube, reciprocating piston or other mechanism. However, a distinguishing feature of the apparatus of FIG. 9, according to embodiments of the present invention, is the inclusion of a valve on the outlet to vacuum and regulation of that valve in response to pressure measured at the tracheal outlet. Other forms of ventilation with active deflation (HFOV and ventilation with NEEP) apply vacuum pressure in such a manner as to decrease tracheal pressure below atmospheric pressure. Such forms of ventilation do not maintain PEEP. The apparatus of the present invention, by applying vacuum pressure at the exit of the breathing circuit, downstream in the expiratory circuit from the trachea, and terminating vacuum application when tracheal pressure decreases to the desired PEEP level, enables deflation to be actively accelerated while maintaining PEEP in the lung.

3. Vibration or Step or Impulse Force Application to the Lung

Lung motion during breathing is normally smooth. Application of vibration or of step or impulse force to the edematous lung could perturb surface tension within edematous alveoli in such a fashion as to facilitate equitable edema liquid distribution.

Figure 13A:
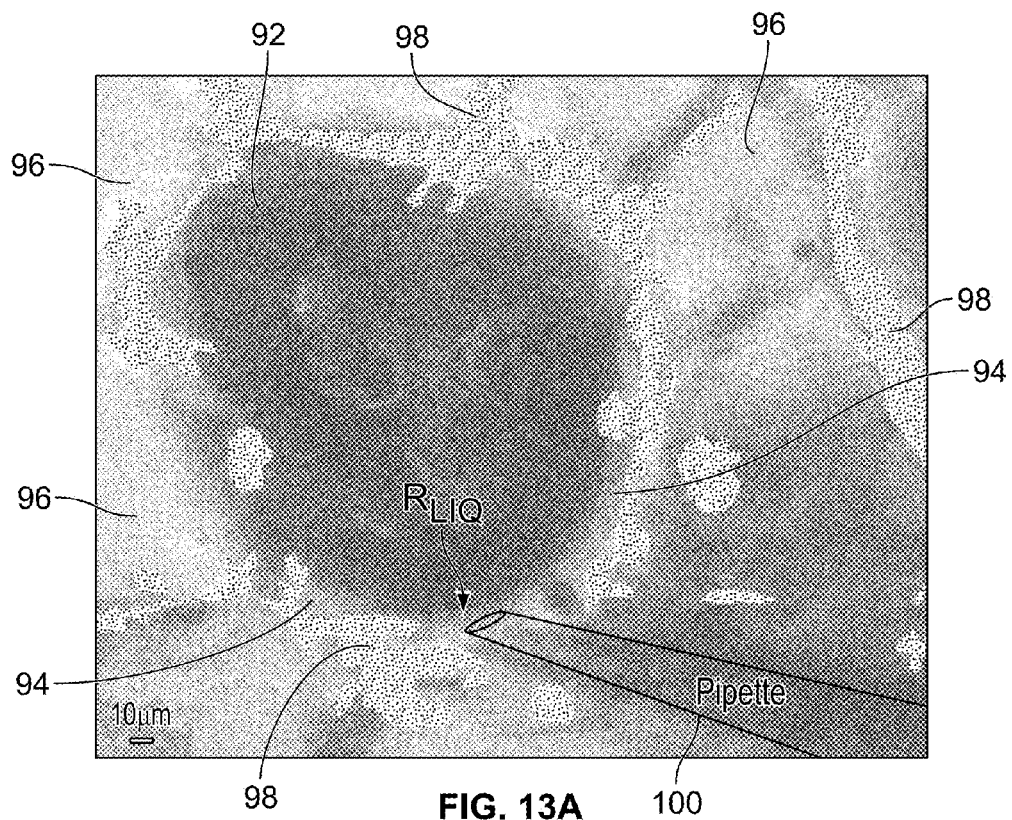
FIGS. 13A and 13B are a pairing of an enhanced micrograph and a graph indicating that surface tension is spatially uniform.
Figure 13B:
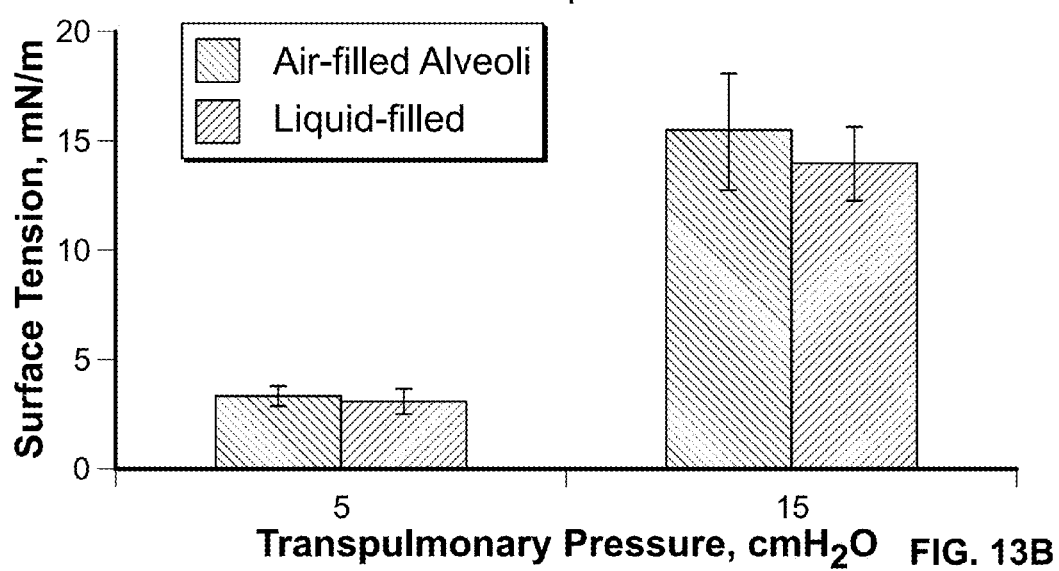

Surface tension is normally spatially uniform in the lung. FIGS. 13A and 13B are a pairing of an enhanced micrograph demonstrating how surface tension is determined in an air-filled alveolus and a graph indicating that surface tension is spatially uniform. The micrograph is an image of an air-filled alveolus 92, with a liquid lining layer 94, surrounded by edematous alveoli 96. Alveolar walls 98 are indicated by light stippling. The pipette measures the liquid lining layer pressure in the air-filled alveolus 92 for surface tension determination according to the Laplace relationship. The graph presents grouped surface tension data for adjacent air- and liquid-filled alveoli (n=3), showing that surface tension does not vary spatially even in a region of heterogeneous alveolar flooding.

Lung vibration could alter the normally uniform surface tension distribution. FIGS. 12C, 12D, and 12E are a group of schematic drawings indicating a conceptual model of vibration effects on edematous alveolar surface tension. Liquid 80 fills the area between the alveolar wall 82 and the air-liquid interface 84. Referring to FIG. 12C, at a normal breathing frequency (0.2 Hz), surfactant distribution and surface tension are constant along the interface 84. Referring to FIG. 12D, a rightward lateral vibration stroke propels the center of the liquid mass 80 to the right because of inertia, and skews the interface 84 to the right such that the interfacial radius R at the right is greater than the radius r at the left. The movement of the liquid 80 compresses the surfactant and lowers surface tension t at the right, and dilates the surfactant and raises the surface tension T at the left, thus generating a tension force to the left. Due to the Laplace law, liquid pressure $P_{LIQ}$ at the right is greater than pressure $p_{LIQ}$ at the left, thus a net pressure force also acts to the left. Just as interplay between inertia and pressure can cause a resonant "rocking mode" during vibration of a pure water droplet, interplay between inertia, surface tension and pressure has the capacity to generate a "rocking mode" in an edematous alveolus, as depicted in FIG. 12D. Higher frequency vibration, likewise due to the interplay of inertia, surface tension, and pressure, has the potential to generate resonant capillary waves. Referring to FIG. 12E, such resonant capillary waves 86 would compress the surfactant and lower surface tension at the crests 88 of the waves 86 and dilate the surfactant and raise tension at troughs 90 of the waves 86. By the Laplace relationship, the pressure below the troughs 90 would be less ($p < P_{ALV}$) than the pressure below the crests 88 ($P > P_{ALV}$).

If surface tension gradients existed along the interface 84, however, they would apply shear stress to, and cause movement of, the liquid 80 below in the interface 84. Thus, vibration of the lung, or application of a step or impulse force to the lung, would generate surface tension gradients at the air-liquid interface 84, and accompanying pressure gradients in the edema liquid 80 below the interface 84. Such induced spatial variation in the surface tension or pressure has the potential to overcome, at random, the pressure barrier trapping liquid in discrete alveoli, therefore to promote clearance of edematous alveoli.

Edematous alveolar liquid pressure is normal maximal at the edge of the alveolus. In the liquid flooded alveolus, liquid pressure $P_{LIQ-BORD}$ at the edge of the alveolus exceeds liquid pressure $P_{LIQ-EDEM}$ in the center of the alveolus (see FIG. 1). Between the two locations, pressure may be assumed to vary smoothly, governed by the smooth variation in interfacial curvature. Perturbation of the normal smooth breathing motion, however, might perturb the typical pattern of pressure variation in edema liquid and cause pressure at the edge of the alveolus transiently to fall below pressure in the center of the alveolus. Referring to FIG. 12A, computation fluid dynamics modeling indicates that such a transient reversal of the pressure barrier is possible. FIGS. 12A and 12B show modeling predictions for effects of lung vibration on edematous alveolar liquid pressure distribution. In the computation fluid dynamic model (Star-CCM+) of FIGS. 12A and 12B, an alveolus is approximated as a 100 micron diameter 3-D sphere with three-quarters of its volume filled with water. Air pressure is modeled at 15 cmH$_2$O). Surface tension is modeled at 15 mN/m, with liquid slipping at the boundary. In FIGS. 12A and 12B, the simulated pressure increases from the darker shading to the lighter shadings. In the simulation, the alveolus was vibrated at 100 Hz, and 45 deg angle. The dashed circles highlight pressure at what would be the border with an adjacent alveolus. Liquid pressure is generally highest at the border, as in FIG. 12A, but sometimes decreases, as in FIG. 12B. Thus, the normal pressure distribution could be inverted independent of any perturbation to interfacial curvature or surface tension. Such a reversal of pressure gradient could, transiently, overcome the pressure barrier $\Delta P_{BARRIER}$ and facilitate clearance of the edematous alveolus.

When vibrating the lung from its periphery, sufficient amplitude is required to overcome damping as the signal propagates. A high frequency signal will travel better through water than air. Thus, the more edematous the lung, the more effective vibration will be as a therapy. In a droplet of pure water as small as an alveolus, the first resonant (rocking) mode would be expected to occur at about 5000 Hz. With the particular geometry of the edematous alveolar interface and inclusion of surfactant at the interface, the resonant frequency is not known, and, in view of the current state of art, is likely to require empirical investigation. Further, even non-resonant vibration could alter the normal edema liquid pressure distribution in a manner that favor alveolar clearance.

Given the tradeoff between amplitude and frequency, initial tests were performed in the relatively low frequency range of 100-200 Hz. With the local edema model and with the global permeability edema model, vibration of the lung was tested for its ability to clear liquid-filled alveoli. A function generator was used to drive a speaker coil and the speaker cone was placed in contact with the lung surface, separated from the lung by saran wrap. As a control, the speaker cone was pressed against the lung surface with the same force as in the test, but in the absence of power to the speaker, such that the speaker cone did not vibrate. As discussed below with relation to FIGS. 14A, 14B, 14C, and 14D, vibration was found to induce equitable edema liquid redistribution in both edema models.

Figure 14A:
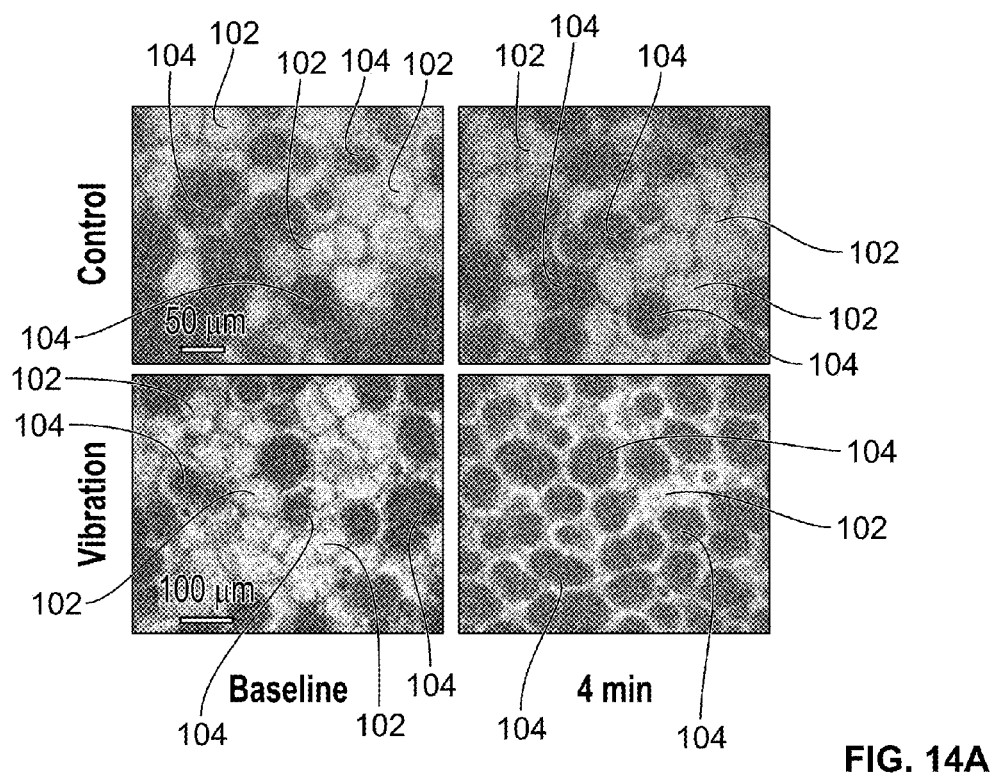
FIGS. 14A and 14B are a pairing of a set of micrographs and a graph illustrating alveolar liquid clearance by vibration of the lung surface in a local edema model according to an embodiment of the present invention.
Figure 14B:
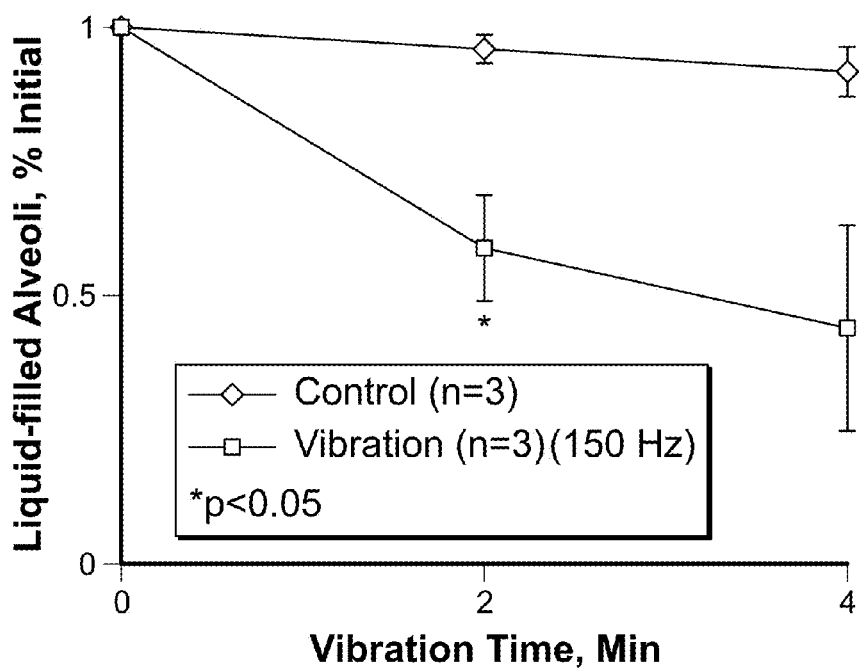
Figure 14C:
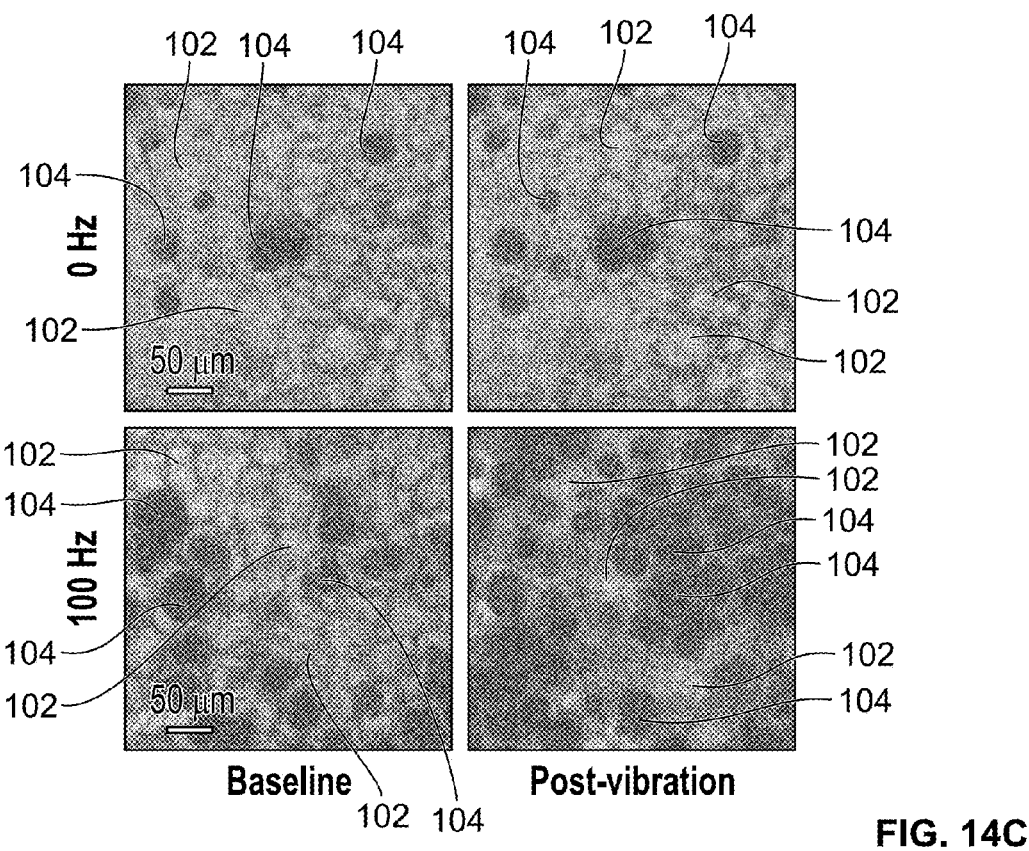
FIGS. 14C and 14D are a pairing of a set of micrographs and a graph illustrating alveolar liquid clearance by vibration of the lung surface in a global permeability edema model according to another embodiment of the present invention.
Figure 14D:
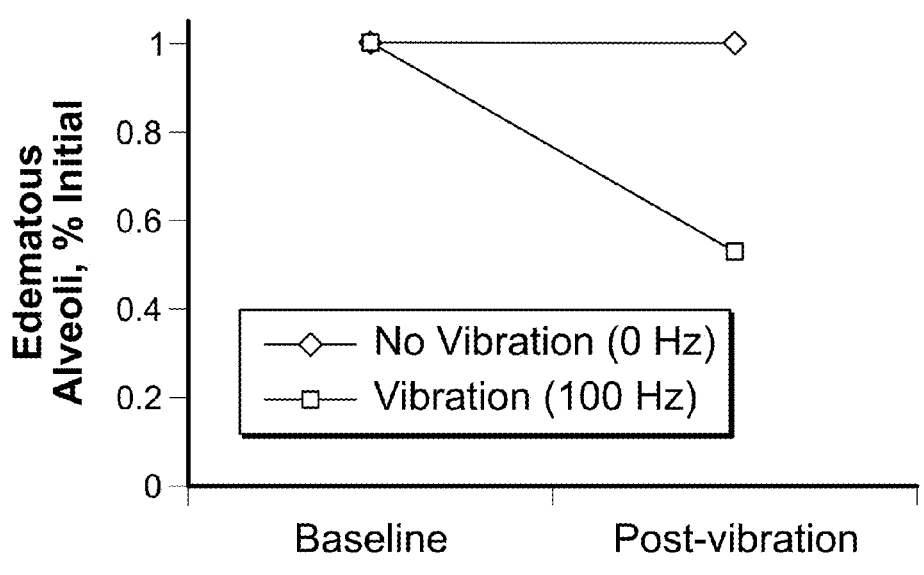

FIGS. 14A and 14B are a pairing of a set of micrographs with a graph indicating that that vibration of the lung surface promotes alveolar liquid clearance, as are FIGS. 14C and 14D. FIGS. 14A and 14B show vibration results in the presence of a local edema model. The edema liquid is 5% albumin in normal saline with 32 μM BCECF. To clear unstable alveoli, the lung is ventilated with 20 sinusoidal cycles between 5 and 15 cmH$_2$O at 0.2 Hz prior to baseline (cycle 0). The micrographs of FIG. 14A include images of the edematous area at baseline and after four minutes of being pressed against a speaker coil (separated by saran wrap) while speaker is unpowered (control) or vibrating at 150 Hz (vibration). The lung was constantly inflated to $P_{ALV}$ of 15 cmH$_2$O during the experiment. It can be seen that vibration effectively clears the alveoli. FIG. 14B presents the results graphically. FIGS. 14C and 14D present the results of the same experiment as that of FIGS. 14A and 14B, replicated in a global permeability edema model with fluorescein (36 μM) included in the perfusate. The lung was vibrated at 100 Hz for 2 min, while held at constant $P_{ALV}$ of 15 cmH$_2$O. It can be seen that vibration effectively clears the alveoli in this model also. In FIGS. 14A and 14C, liquid-filled alveoli 102 are shown as light or medium gray areas, and air-filled alveoli 104 are shown as darker areas 104.

To apply vibrations of ≥50 Hz to the lung for edema clearance, the following methods could be employed individually, in combination and/or in conjunction with mechanical ventilation; non-invasive ventilation; or lung expansion devices including chest physiotherapy devices and high frequency oscillation devices, according to various embodiments of the present invention:

1. Coupling a speaker coil, oscillator or ultrasound generator to the patient's chest wall or back;
2. Implanting a speaker coil, oscillator or ultrasound generator in the fluid-filled plural space (outside the lungs, inside the ribcage);
3. Inserting a fluid-filled conduit into the pleural space and, via the conduit, hydraulically applying a high frequency pressure signal to the pleural fluid, with, e.g., a speaker coil, oscillator or an ultrasound generator;
4. Coupling a speaker coil, oscillator or ultrasound generator to the trachea, either directly or through the skin;
5. Percussing the chest and/or back with a commercially-available device intended for that purpose (e.g., a pneumatic vest); and
6. Adding a ≥50 Hz component to an existing ventilation pressure, volume or flow waveform.

In some embodiments of the invention, a step or impulse force could be applied to the lung, rather than a vibration. In ideal form, step and impulse functions are of infinite frequency. The actual frequency of force application to the lung would not be infinite, but would be maximal. Thus, repetitive application of a step or impulse force to the lung would promote edematous alveolar clearance. A step or impulse function would be employed alone or in conjunction with mechanical ventilation; non-invasive ventilation; or lung expansion devices including chest physiotherapy devices and high frequency oscillation devices, by one of the following methods:

1. Any of the mechanisms discussed above with respect to vibration of the lung at high frequency;
2. Any of the mechanisms for sudden deflation discussed in Section 2; and
3. Transient airway occlusion during deflation, particularly in combination with active, accelerated deflation. Transient airway occlusion could be effected with transient closure of a valve at airway exit; a spinning ball or high frequency flow interrupter, such as are used in high frequency percussive ventilation; or other mechanism. Deflation could be accelerated by any of the mechanisms discussed in Section 2; by use of a Hayek Oscillator; or by other means.

It will be understood that the embodiments described herein are merely exemplary and that a person skilled in the art may make many variations and modifications without departing from the spirit and scope of the invention. All such variations and modifications are intended to be included within the scope of the invention described in the claims appended hereto.

I claim:

1. A method of treating edema in an edematous lung containing regions with heterogeneous alveolar flooding by alveolar liquid, the method comprising delivering to the alveolar liquid at least one additive that decreases surface tension of the alveolar liquid, thereby lowering the surface tension of the alveolar liquid so as to promote equitable redistribution of the alveolar liquid among alveoli of the lung, wherein the at least one additive includes at least one rhodamine dye comprising an iminium cation, wherein said delivering step increases the amount of the rhodamine dye in the alveolar liquid to a concentration of 1.0 µM.

2. The method of claim 1, wherein said delivering step is performed such that the lowered surface tension of the alveolar liquid directly lessens ventilation-induced over-expansion injury of aerated alveoli located adjacent to the flooded alveoli.

3. The method of claim 1, wherein the at least one rhodamine dye includes at least one of sulforhodamine B or rhodamine WT.

4. The method of claim 1, wherein said delivering step comprises instilling a solution containing the at least one additive into a trachea or bronchus of a patient having the regions with the heterogeneous alveolar flooding by the alveolar liquid in the lung.

5. A method of treating edema in an edematous lung containing regions with heterogeneous alveolar flooding by alveolar liquid, the method comprising delivering to the alveolar liquid at least one additive that decreases surface tension of the alveolar liquid, thereby lowering the surface tension of the alveolar liquid so as to promote equitable redistribution of the alveolar liquid among alveoli of the lung, wherein the at least one additive includes at least one rhodamine dye comprising an iminium cation, wherein the delivering step comprises administering a solution containing the at least one additive into a patient having a circulatory system and the regions with heterogeneous alveolar flooding by the alveolar liquid in the lung by injecting the solution into the circulatory system of the patient.

6. The method of claim 5, wherein said delivering step is performed such that the lowered surface tension of the alveolar liquid directly lessens ventilation-induced over-expansion injury of aerated alveoli located adjacent to the flooded alveoli.

7. The method of claim 5, wherein the at least one rhodamine dye includes at least one of sulforhodamine B or rhodamine WT.

8. The method of claim 5, wherein said delivering step increases the amount of the rhodamine dye in the alveolar liquid to a concentration of 1.0 µM.

* * * * *